United States Patent [19]

Bergmann et al.

[11] Patent Number: 5,077,040
[45] Date of Patent: Dec. 31, 1991

[54] HAIR-TREATING MICROEMULSION COMPOSITION AND METHOD OF PREPARING AND USING THE SAME

[75] Inventors: Wolfgang Bergmann, Highland Park; Janice Bees, Libertyville, both of Ill.

[73] Assignee: Helene Curtis, Inc., Chicago, Ill.

[21] Appl. No.: 516,445

[22] Filed: Apr. 30, 1990

[51] Int. Cl.$^5$ .................. A61K 7/075; A61K 7/08; A61K 7/11

[52] U.S. Cl. .................. 424/70; 424/71; 252/DIG. 13; 252/550; 252/558; 252/174.21

[58] Field of Search .................. 424/70, 71, 83, 78, 424/80, 81; 252/DIG. 13, 550, 553, 558, DIG. 1, 544, 174.15, 174.21

[56] References Cited

U.S. PATENT DOCUMENTS 4,960,588 10/1990 Hoshowski et al. .............. 424/70 X Primary Examiner—Thurman K. Page
Assistant Examiner—Susan S. Rucker
Attorney, Agent, or Firm—Marshall, O'Toole Gerstein, Murray Bicknell

[57] ABSTRACT

A microemulsion composition for treating the hair, comprising a water-insoluble amino-containing compound, such as an amine or an amino-functionalized silicone; an ionizable metal salt, wherein the metal has a valence of at least II, such as magnesium chloride or zinc chloride; an ester compound having the general structural formula $$R_1-O-(A)_X-CH_2CO_2R_2,$$

wherein $R_1$ is an alkyl group including from about eight to about 18 carbon atoms, $R_2$ is an alkyl group including from one to about four carbon atoms, A is an alkylene oxide moiety wherein the alkylene group includes from one to about four carbon atoms, and X is a number in the range of from about 4 to about 20; and water, and wherein the composition has a pH of less than 7 and a particle size in the range of from about 0.1 nm to about 250 nm, to impart durable conditioning properties to treated hair is disclosed.

54 Claims, 11 Drawing Sheets

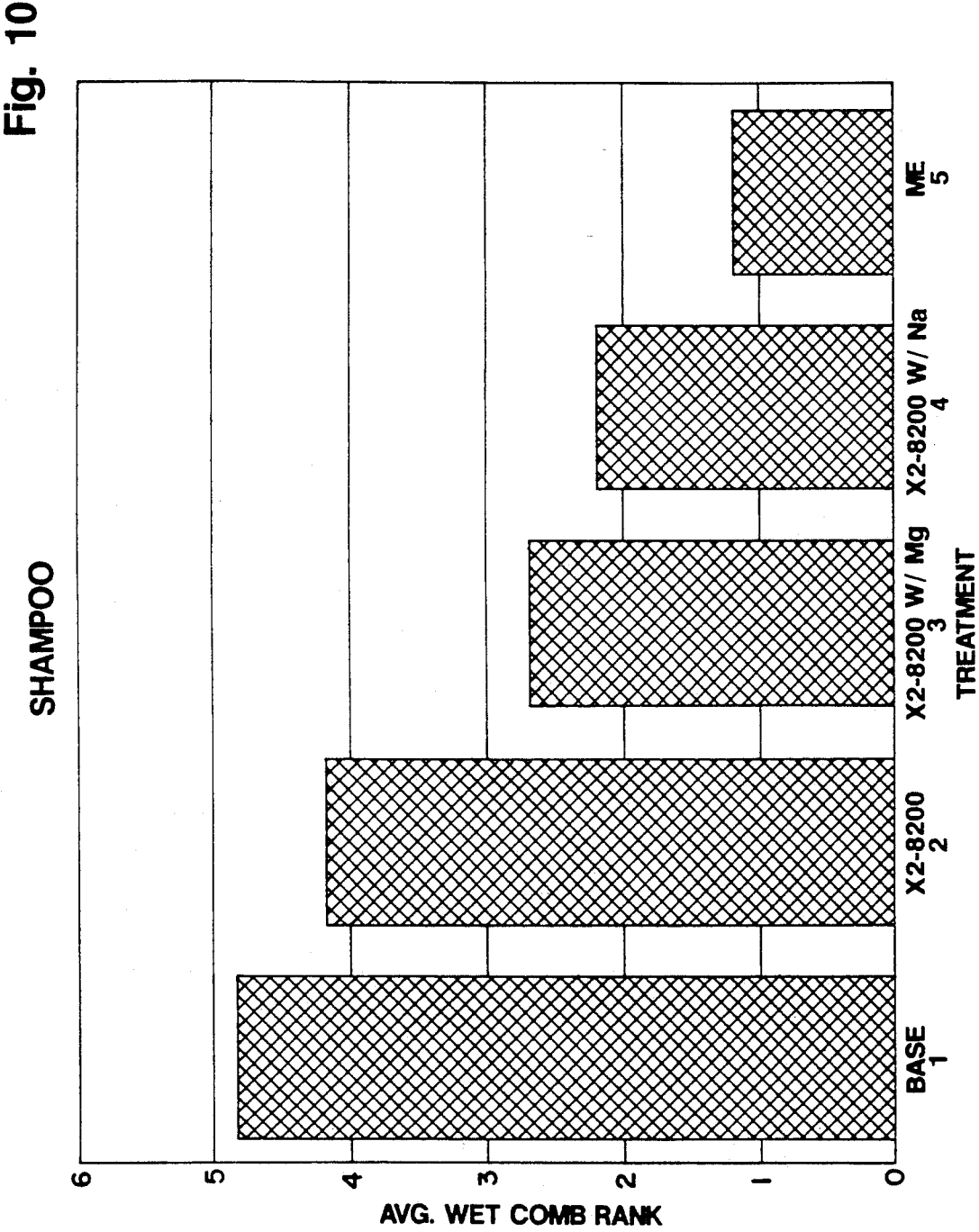

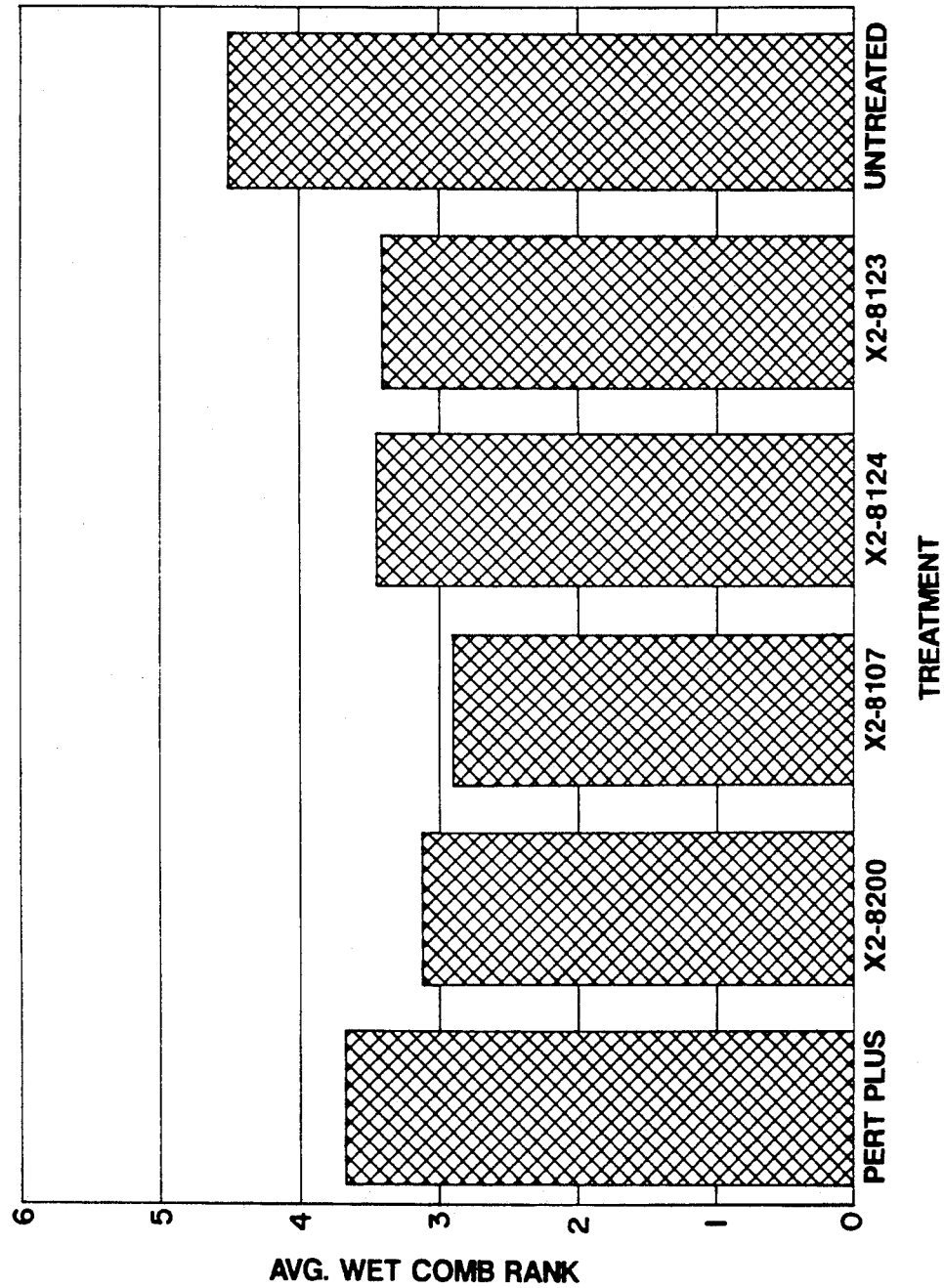

HAIR-TREATING MICROEMULSION COMPOSITION AND METHOD OF PREPARING AND USING THE SAME

FIELD OF INVENTION

The present invention relates to a hair-treating microemulsion composition, to a method of preparing the microemulsion composition and to a method of treating human hair that imparts improved physical and esthetic properties to the treated hair. More particularly, the present invention is directed to a microemulsion composition including a water-insoluble amino-containing compound, such as an amine or an amino-functionalized silicone; and an ionizable metal salt, wherein the metal has a valence of at least II, such as magnesium chloride or zinc chloride, and wherein preferably, the molar or molar-equivalent ratio of ionizable metal salt to water-insoluble amino-containing compound of at least 1:1; an ester compound having the general structural formula $$R_1-O-(A)_X-CH_2CO_2R_2,$$

wherein $R_1$ is an alkyl group including from about eight to about 18 carbon atoms, $R_2$ is an alkyl group including from one to about four carbon atoms, A is an alkylene oxide moiety wherein the alkylene group includes from one to about four carbon atoms and X is a number in the range of from about 4 to about 20; and water. The microemulsion composition has a pH of less than 7, and a pH preferably in the range of from about 3 to about 6.8; and a particle size in the range of from about 0.1 nm (nanometers) to about 250 nm, and usually less than about 100 nm, and is used to impart improved and durable conditioning properties to treated hair. The microemulsion composition of the present invention can be applied to the hair from an aqueous solution, aqueous-alcoholic mixture, aqueous spray, aerosol, mousse, conditioner, fixative, shampoo-conditioner or other similar hair-treatment or hair-styling product.

BACKGROUND OF THE INVENTION

Hair that has been thoroughly cleansed, but not conditioned, is extremely difficult to comb, in either the wet or dry state, because the individual hair fibers tend to snarl, kink, and interlock with each other. Incompletely dried hair, such as towel dried hair, has poor brushing properties, then, even after complete drying, the combing and brushing properties of the hair remains poor. Often, the hair also has undesirable electrostatic properties in a low humidity atmosphere that causes the hair to "fly away", thereby further reducing the esthetic properties of the hair. In addition, normal hair can be so fine, limp and lacking in body that the hair does not hold a hair set well. Also, the hair can lose body and can be weakened further by being subjected to chemically-active hair treatments such as permanent waves and tints. The hair can be weakened even further by other contributing factors, such as bleaching by sun exposure or chlorinated swimming pool water, wind, pollution, and the like.

Normal hair is usually hydrophobic. However, many hair-treating compositions remove the natural hydrophobic components from the hair. As a result, the hydrophobicity of the hair decreases, the relative porosity of the hair increases and the hair tends to absorb water and swell more readily. In such a weakened and porous state, the water-swollen hair is more vulnerable to stretching and breaking. Therefore, investigators have sought to counteract the unmanageability of thoroughly cleansed hair by utilizing compositions containing various conditioning compounds. When applied to the hair, these compositions demonstrated varying abilities to improve the manageability and the physical and esthetic properties of the hair.

Accordingly, investigators have found compositions and formulation techniques to provide a hair-treating product that imparts beneficial hair conditioning properties such as improved manageability, easy application and combing, quick drying and non-stickiness, good hair body and bounce, increased hair volume and gloss, and hydrophobicity. It is evident that in the formulation of any end-use product, some of these benefits are sacrificed to some degree to achieve a competing benefit. Therefore, the formulation of hair conditioning products has proved difficult. As a result, hair conditioning products have been developed in a variety of product forms. For example, hair conditioning products are available as gels, aerosol foams, all-purpose lotions, hair sprays, holding lotions, conditioners and shampoos. However, in using presently available commercial products, consumers must sacrifice certain desirable physical or esthetic hair properties in order to achieve or improve other desirable physical or esthetic properties.

Consequently, the present invention relates to a composition and method of treating the hair that improve the physical and esthetic properties of the treated hair. It has been found that by treating the hair with a microemulsion composition including a water-insoluble amino-containing compound; an ionizable metal salt, wherein the metal has a valence of at least II; an ester compound of the general structural formula:

$$R_1-O-(A)_X-CH_2CO_2R_2;$$

and water, the physical and esthetic properties of the hair are improved, such that the hair demonstrates durable conditioning properties such as wet and dry combing, body and manageability. Thus, the improved physical and esthetic properties imparted to the hair upon treatment with a composition of the present invention obviates the need to treat the hair each day or after each shampooing.

Therefore, the present invention is directed to a hair-treating composition, in the form of a stable, translucent or transparent microemulsion that has demonstrated an improved ability to deposit conditioning agents onto the hair, and an improved durability of conditioning agents deposited on the hair; has improved the wet and dry combing of treated hair; and has imparted satisfactory, and durable, esthetic and physical properties to freshly-cleaned and dried hair, including, in particular, combing, manageability, body and shine. The microemulsion compositions of the present invention are exceptionally stable and can be formulated into a variety of hair care products, including conditioning shampoos, conditioners, mousses, fixatives, lotions, hair sprays, gels, and similar hair-treating and hair-styling products.

In general, emulsions are classified as macroemulsions or as microemulsions depending upon the droplet size of the liquid present in the internal, or dispersed, phase of the emulsion. Macroemulsions, having droplets with an average diameter of from about 10 microns to about 1000 microns, do not permit light to pass through the emulsion. Therefore, macroemulsions typically appear milky white. Microemulsions, however, are stable compositions including internal phase droplets that are significantly smaller than the droplets in the internal phase of macroemulsions, and having an approximate average diameter of less than about 150 nm. Microemulsions are generally more stable than macroemulsions, and typically are translucent, and often transparent, in nature.

Emulsions also are classified further depending on the nature of the liquid forming the internal, or dispersed, phase and the nature of the liquid forming the external, or continuous, phase. An emulsion wherein a water-insoluble compound, like an oil, is dispersed as droplets throughout a continuous aqueous phase is termed an oil-in-water emulsion. However, if water is the dispersed phase and an oil is the continuous phase, the emulsion is termed a water-in-oil emulsion. Whether the aqueous phase or the oil phase is the dispersed phase or the continuous phase depends primarily on the emulsifying agent, or agents, used, and the relative amounts of the two liquid phases. The microemulsions of the present invention preferably are oil-in-water microemulsions, wherein the continuous phase is water. However, water-in-oil microemulsion compositions also are useful in the method of the present invention.

Accordingly, the present invention relates to a microemulsion composition and method of treating the hair that improve the physical and esthetic properties of the treated hair. It has been found that by treating the hair with a microemulsion composition including a water-insoluble amino-containing compound, such as an amine or an amino-functionalized silicone compound, like trimethylsilylamodimethicone; an ester compound having the general structural formula:

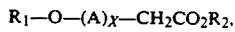

like isopropyl $C_{12-15}$ pareth-9-carboxylate; an ionizable metal salt, wherein the metal has a valence of at least II, like magnesium chloride; and water, the physical and esthetic properties of the treated hair are improved such that the hair is conditioned and demonstrates durable conditioning properties.

Various effects resulting from treating human hair with metal salts or amines are known. For example, polyvalent metal salts are known in the art for their astringent and antiperspirant effects on skin. Hewitt et al., in U.S. Pat. No. 3,842,847, taught the use of astringent water-soluble salts of aluminum, hafnium, zirconium, zinc and like metals in a shampoo and hair treatment to diminish scalp perspiration. Hewitt et al. also reported antistatic and anti-soiling effects on hair treated with aqueous rinses including aluminum chlorohydrate. Hewitt et al. theorized that the astringent metal salt reacted with the hair keratin to reduce the anionic nature of the hair, and therefore, to reduce "fly-away" hair. However, to obtain the benefits disclosed by Hewitt et al., the hair had to be water rinsed after treatment until the pH of the rinse water was at least over 6. In contrast, to achieve the benefits of improved conditioning, the microemulsion composition of the present invention does not have to be rinsed from the hair.

Cassidy, in U.S. Pat. No. 3,208,910, disclosed the use of a water-soluble zirconium carboxylate salt in a hair styling fluid to impart body, moisture resistance and sheen to human hair. Zirconium acetate, present in a concentration of 0.1 percent to 2 percent in a composition having a pH from about 3 to about 6, was used in a treatment for setting the hair. However, the treated hair behaved as if it were full of snarls and the hair was extremely difficult to comb when the concentration of zirconium acetate exceeded 2 percent. Consequently, body-enhancing and moisture-resistance effects could be imparted only by including auxiliary dispersing agents, like waxes and polymers; or by washing the hair with a soap-based shampoo to form an insoluble zirconium soap on the hair. However, in accordance with the present invention, the absolute concentration of the water-soluble metal salt is not limited and auxiliary agents, except for the water-insoluble amino-containing compound, are not required to produce the new and unexpected results of the present invention.

Similarly, Anzuino and Robbins, in the publication "Reactions of Metal Salts with Human Hair Containing Synthetic Polymers", *J. Soc. Cosmet. Chem.*, 22, pp. 179-186 (1971), taught the polymerization of vinyl monomers, such as methacrylic acid or N,N-dimethylaminoethyl methacrylate, within the keratin fibers of the hair to alter the chemical reactivity of the keratin. Then the polymer-containing hair fibers were reacted with metal salts, such as calcium chloride, nickel chloride, or zinc acetate, to improve the wet load extension properties of the hair. However, the method disclosed by Anzuino and Robbins involves a chemical reduction of the hair that imparts roughness, color lightening and other undesirable properties to the hair. In contrast, the composition and method of the present invention does not require a chemical reduction of the hair fiber and, rather than adversely affecting the hair, imparts improved and durable conditioning properties to the hair.

Homan, in U.S. Pat. No. 4,487,883, disclosed the use of a polymer having at least one nitrogen-hydrogen bond and an anhydrous additive, like a titanate, zirconate, or vanadate, in a hair-treating composition. According to the teachings of Homan, after application to the hair, the polymer is crosslinked upon exposure to moisture or humidity to provide hair conditioning and a hair set. A subsequent shampooing breaks the crosslinking bond, and the polymer, now in its original form, still acts as a conditioner, but does not maintain the hair set. However, the compositions disclosed by Homan suffer from the disadvantage of requiring storage in an anhydrous state. Such storage conditions usually are not practically feasible because it is difficult to insure that a commercial product remains moisture-free under normal production and storage conditions. Conversely, the microemulsion composition of the present invention is not limited to polymeric nitrogen-containing compounds, and the microemulsion composition has an aqueous base, thereby allowing normal production and storage conditions and a variety of formulation choices.

Similarly, European Patent Application No. 0117360 teaches the use of an aqueous composition including an emulsified polymer having at least one nitrogen-hydrogen bond and an organic zirconate, germanate and/or titanate, and having a pH of 6 to 8, in a process to condition and set the hair. The method and composition disclosed in European Patent Application 0117360 differs from the present invention in that the European disclosure operates well outside the pH range of the present invention and, more importantly, the composition utilizes nitrogen-containing polymers and organometallic compounds.

In U.S. Pat. No. 4,283,384, Jacquet et al. disclosed a composition including a particular type of polymer produced from an unsaturated monomer such as acrylic acid, a compound containing at least one hydroxyl functionality such as polyvinyl alcohol or pentaerythritol, and cerium ion. The polymer imparts good holding power to hair when the polymer is applied to the hair in a shampoo formulation. In the method of Jacquet, the cerium ion apparently is not involved in the interaction between hair and polymer. Furthermore, Jacquet et al. do not teach or suggest that the disclosed composition imparts a durable hair conditioning properties to the hair. In contrast, the present invention imparts conditioning properties to the hair, and exhibits unexpected conditioning durability, by efficiently depositing the conditioning agents on the hair.

In U.S. Pat. No. 4,614,200, Hsiung et al. disclosed utilizing an aqueous aluminum salt solution, without an amino-containing compound, to improve the set retention properties of hair at an ambient relative humidity of 50–60%. Hsiung et al. also taught that a polyvalent metal salt can be included in a standard hair conditioning formulation including a quaternary ammonium compound and a fatty amide compound to improve the conditioning properties of the hair. However, Hsiung et al. neither teach nor suggest using a metal salt in a clear microemulsion composition, further including an ester compound of structural formula $$R_1-O-(A)_x-CH_2CO_2R_2$$

and a water-insoluble amine or amino-functionalized silicone, to impart improved and durable conditioning properties to treated hair. As will be demonstrated more fully hereinafter, a fatty amide compound and a quaternary ammonium compound do not impart the improved esthetic and physical properties to hair that are imparted by a water-insoluble amino-containing compound, and a metal salt having a valence of at least II.

Abegg et al. in U.S. Pat. No. 3,958,581, disclosed a hair-treating composition including a divalent metal salt and a cationic polymer. Abegg et al. disclosed only the use of water-soluble cationic polymers having at least one tertiary amine or quaternary ammonium group in the polymeric chain and having a molecular weight of between about 1000 and 3,000,000. In contrast, the microemulsion composition and method of the present invention utilize water-insoluble monomeric primary, secondary and tertiary amines having a molecular weight substantially less than about 1000, or an amino-functionalized silicone polymer having only primary or secondary amino groups. Abegg et al. do not teach or suggest that a water-insoluble monomeric primary, secondary or tertiary amine having a molecular weight less than about 1000, or that an amino-functionalized silicone polymer including only primary or secondary amino groups, can be used with a divalent metal ion to impart improved physical or esthetic properties to the hair.

As also will be demonstrated more fully hereinafter, an important water-insoluble amino-containing compound useful in the composition and method of the present invention is an amino-functionalized silicone, like trimethylsilylamodimethicone. Silicone emulsions and microemulsions are well-known in the art of treating hair, but each known reference fails to teach or suggest that a stable microemulsion composition, suitable for treating hair, can be produced in a one-step process from a combination of a metal ion having a valence of at least II, a water-insoluble amino-containing compound, an ester compound of general structural formula $$R_1-O-(A)_x-CH_2CO_2R_2$$

and water.

For example Rosano, in U.S. Pat. No. 4,146,499, utilizes two surfactants in a four-step process of preparing an oil-in-water microemulsion. Rosano, in U.S. Pat. No. 4,472,291, also discloses the preparation of an oil-in-water microemulsion from a sole surfactant that has an electrostatic charge on the hydrophilic moiety of the surfactant. The viscosity of this microemulsion can be increased by adding a second surfactant to the microemulsion. In contrast, the method and composition of the present invention requires only a single, ester compound to form the microemulsion in a one-step process. Furthermore, and as will be demonstrated more fully hereinafter, a stable microemulsion composition of the present invention is formed regardless of the order of addition of the essential ingredients and is formed by employing a relatively low amount of the ester compound, such as from about 0.05% to about 15% by weight of the composition.

U.S. Pat. No. 4,388,437 to Ona discloses an emulsified composition including an amino-functionalized silicone and an organtitanate useful for treating fibers. The Ona composition does not include an ionizable metal salt or an ester compound having the general structural formula $$R_1-O-(A)_x-CH_2CO_2R_2.$$

In addition, Ona does not disclose that the composition is a microemulsion having a small droplet particle size or that the composition is useful to impart durable conditioning properties to hair.

Other patents disclosing emulsions including an amino-functionalized silicone include DeMarco et al. U.S. Pat. No. 4,529,586, wherein amodimethicone is emulsified with a cationic emulsifier to increase the effectiveness of a cationic hair conditioning compound. The present invention does not rely upon cationic polymer to impart conditioning properties to the hair. Chandra et al. in U.S. Pat. No. 4,559,227 discloses a solution or microemulsion of an amino-functionalized silicone achieved by using an anionic surfactant in conjunction with an alkanolamide or an amine oxide. Neither patent discloses the use of an ionizable metal salt nor the particular ester compounds utilized in the present invention as the sole emulsifier in a one-step process to provide a microemulsion composition useful for treating human hair.

In addition, Kohl et al. U.S. Pat. No. 4,749,732 discloses hair care uses of polydiorganosiloxanes containing aminoalkyl groups modified by alkoxycarbonylalkyl substituents. Kohl et al. modify the amino-functionalized silicone to reduce or eliminate incompatibility of the functionalized silicone with other composition ingredients. However, the stable microemulsion compositions of the present invention effectively isolate the functionalized silicone from other composition ingredients, like anionic surfactants, thereby precluding the need to modify the functionalized silicone. U.S. Pat. No. 4,563,347 to Starch discloses the use of amino-functionalized silicones in hair conditioning compositions to improve combing and feel characteristics. U.K. Patent Application Nos. 2,157,168 and 2,143,434 disclose the use of amino-functional silicones in hair care formulations such as a shampoo, a rinsed or a non-rinsed lotion, a restructuring composition, a composition for blow drying, and a composition for permanent waving. However, none of the references disclose or suggest the composition of the present invention or the use of an amino-functionalized silicone in a microemulsion composition.

Linn et al. in U.S. Pat. Nos. 4,797,272 and 4,797,273 disclose oil-in-water and water-in-oil microemulsions, including silicones and a relatively high amount of surfactants, such as from about 20% to about 80% by weight, suitable as moisturizers and sunscreens. However, Linn et al. do not suggest using a water-insoluble amino-containing compound, like an amino-functionalized silicone, in combination with a metal having a valence of at least II, in a composition to improve the conditioning properties of treated hair. Blehm et al. in U.S. Pat. No. 4,842,766 disclose microemulsions including amino-functionalized silicones and a cosurfactant having an HLB value of at least one. Blehm et al. require that the silicone-containing compound and the surfactant first be thoroughly admixed to form a clear composition prior to adding water to form the microemulsion. In contrast, the essential ingredients of the present composition can be added in any order to produce a stable, microemulsion composition.

U.S. Pat. No. 4,620,878 to Gee teaches a method of preparing a microemulsion composition from an oil concentrate including a silicon-containing compound having a polar radical, a surfactant that is insoluble in the silicon-containing compound and water. To form a microemulsion, the oil concentrate then is dispersed in a major amount of water. The present invention does not require the formation of an oil concentrate. In contrast, the microemulsion composition of the present invention can be produced directly from the individual essential ingredients.

U.S. Pat. No. 4,960,588 assigned to the same assignee as the present application, discloses a composition including a water-insoluble amino-containing compound, like an amine or an amino-functionalized silicone, and a metal salt useful for treating hair to impart durable hair set retention properties. However, the compositions disclosed in U.S. Pat. No. 4,960,588 were macroemulsions demonstrating varying degrees of stability. For example, large amounts of alcohol were incorporated into the macroemulsions to achieve a suitable degree of stability. In some instances, the amino-containing compound and the metal salt were applied to the hair from different vehicles in order to avoid the stability problems found on these macroemulsions. However, the present microemulsion compositions have overcome the stability problems of the macroemulsions of the prior art, and are useful in treating hair to impart improved and durable conditioning properties to treated hair.

Therefore, overall, not one of the above-discussed references either discloses or teaches a microemulsion composition suitable for treating human hair and comprising a water-insoluble amino-containing compound, like an amino-functionalized silicone or an amine; an ionizable metal salt, wherein the metal has a valence of at least II, like magnesium chloride or zinc chloride; an ester compound having the general structural formula:

$$R_1-O-(A)_x-CH_2CO_2R_2.$$

wherein $R_1$ is an alkyl group including from about eight to about 18 carbon atoms, $R_2$ is an alkyl group including from one to about four carbon atoms, A is an alkylene oxide moiety wherein the alkylene group includes from one to about four carbon atoms and X is a number in the range of from about 4 to about 20; and water, and wherein the composition has a pH of less than 7, and preferably in the range of from about 3 to about 6.8, and a particle size in the range of from about 0.1 nm to about 250 nm, that, after application to human hair, imparts durable hair conditioning properties to the hair.

In contrast, to date, the compositions and methods used to treat and condition hair have suffered from sacrificing one beneficial hair conditioning property in order to achieve another beneficial hair conditioning property or from abnormally long times to treat the hair. Prior to the present invention, no known method or composition has been employed to effectively treat hair with a microemulsion composition within a few minutes to impart excellent and durable hair conditioning properties to hair.

Therefore, in accordance with the present invention, the physical and esthetic properties of hair are surprisingly and unexpectedly improved by contacting the hair with a microemulsion composition including a water-insoluble amino-containing compound, an ester compound having the general structural formula $$R_1-O-(A)_x-CH_2CO_2R_2.$$

and an ionizable metal salt, wherein the metal has a valence of at least II. The microemulsion composition can be applied to the hair from an aqueous or an aqueous/alcoholic vehicle, such as a hair spray, hair shampoo, or hair conditioner, at ambient temperature and is allowed to contact the hair for relatively short times to provide the benefits and advantages of improved physical and esthetic hair properties. Therefore, and as will be demonstrated more fully hereinafter, the method and composition of the present invention provide esthetically-pleasing, hair does not damage the hair and imparts excellent and durable conditioning properties, such as body and manageability, to the hair.

SUMMARY OF THE INVENTION

In brief, the present invention relates to a composition and method of treating hair. More particularly, the present invention relates to a method of treating the hair, whereby contacting the hair with a microemulsion composition including a water-insoluble amino-containing compound; an ionizable metal salt, wherein the metal has a valence of at least II; an ester compound having the general structural formula:

$$R_1-O-(A)_x-CH_2CO_2R_2.$$

wherein $R_1$ is an alkyl group including from about eight to about 18 carbon atoms, $R_2$ is an alkyl group including from one to about four carbon atoms, A is an alkylene oxide moiety wherein the alkylene group includes from one to about four carbon atoms, and X is a number in the range of from about 4 to about 20; and water, maintains and improves the esthetic and physical characteristics of the hair, such as gloss, combability, softness, and body. The compositions of the present invention are stable, translucent or transparent microemulsions having a particle size in the range of from about 0.1 nm to about 250 nm, and usually less than about 100 nm, that demonstrate an improved ability to deposit hair-conditioning compounds onto the hair. Surprisingly and unexpectedly, human hair treated with a stable microemulsion composition of the present invention exhibits substantially improved and durable hair conditioning properties.

Therefore, it is an object of the present invention to provide a microemulsion composition for treating hair.

It is also an object of the present invention to provide an aqueous hair-treating microemulsion composition comprising a water-insoluble amino-containing compound; an ionizable metal salt, wherein the metal salt has a valence of at least II; and an ester compound having the general structural formula $$R_1-O-(A)_x-CH_2CO_2R_2.$$

Another object of the present invention is to provide a hair treating composition having a pH of less than 7, and preferably in the range of from about 3 to about 6.8, and, to achieve the full advantage of the present invention, having the molar quantity of the ionizable metal salt equal to or greater than the molar, or molar-equivalent, quantity of the amino-containing compound.

Another object of the present invention is to provide a method of treating hair with a microemulsion composition to achieve improved and durable hair conditioning properties.

Another object of the present invention is to provide a method of treating hair by contacting the hair with a composition having a pH of less than 7, and including a water-insoluble compound having at least one amino-functionality; an ionizable metal salt, wherein the metal has a valence of II or greater; an ester compound having the general structural formula $$R_1-O-(A)_x-CH_2CO_2R_2.$$

and water, at ambient temperature for a relatively short contact time to achieve a hair set having improved and durable hair conditioning properties.

Another object of the present invention is to provide a method of treating human hair to yield sufficiently conditioned hair by treating the hair with a microemulsion composition including a water-insoluble amino-containing compound and an ionizable metal salt.

Still another object of the present invention is to provide a method of treating the hair to impart durable hair conditioning properties by contacting the hair with a hair spray, a hair conditioner, a hair fixative, a hair shampoo or other hair styling product to treat the hair in either a rinse-off or leave-on method.

Another object of the present invention is to provide a method of treating hair to achieve increased deposition of conditioning agents on the hair and to achieve increased and durable conditioning of hair by contacting the hair with a microemulsion composition comprising:

(a) from about 0.1% to about 6% by weight of a water-insoluble amino-containing compound;

(b) from about 0.005% to about 4% of an ionizable metal salt, wherein the metal has a valence of at least II;

(c) from about 0.05% to about 15% by weight of an ester compound having the general structural formula $R_1-O-(A)_x-CH_2CO_2R_2$, and (d) water, wherein the microemulsion has a pH of less than 7, and wherein the particle size of the microemulsion composition ranges from about 0.1 nm to about 250 nm.

Another object of the present invention is to provide a new and improved microemulsion composition capable of conditioning hair and imparting improved physical and esthetic properties both to normal hair and to tinted, frosted, bleached and other substantially-damaged hair.

BRIEF DESCRIPTION OF THE DRAWINGS

The above and other objects and advantages and novel features of the present invention will become apparent from the following detailed description of the preferred embodiments of the invention illustrated in the accompanying figures illustrating the enhanced hair conditioning properties achieved by using the method and composition of the present invention, wherein:

FIG. 10 is a bar graph comparing the average wet comb rank of hair treated with a base shampoo formulation to a microemulsion composition of the present invention, a shampoo formulation including a water-insoluble amino-containing compound and an ester of structural formula (II), and a shampoo formulation including a water-insoluble amino-containing compound, an ester of structural formula (II) and either a monovalent or a divalent metal ion; and FIG. 11 is a bar graph comparing the average wet comb rank of untreated hair to hair treated with PERT PLUS and with shampoo/microemulsion compositions including different amino-functionalized silicones.

DETAILED DESCRIPTION OF THE INVENTION

Figure 1:
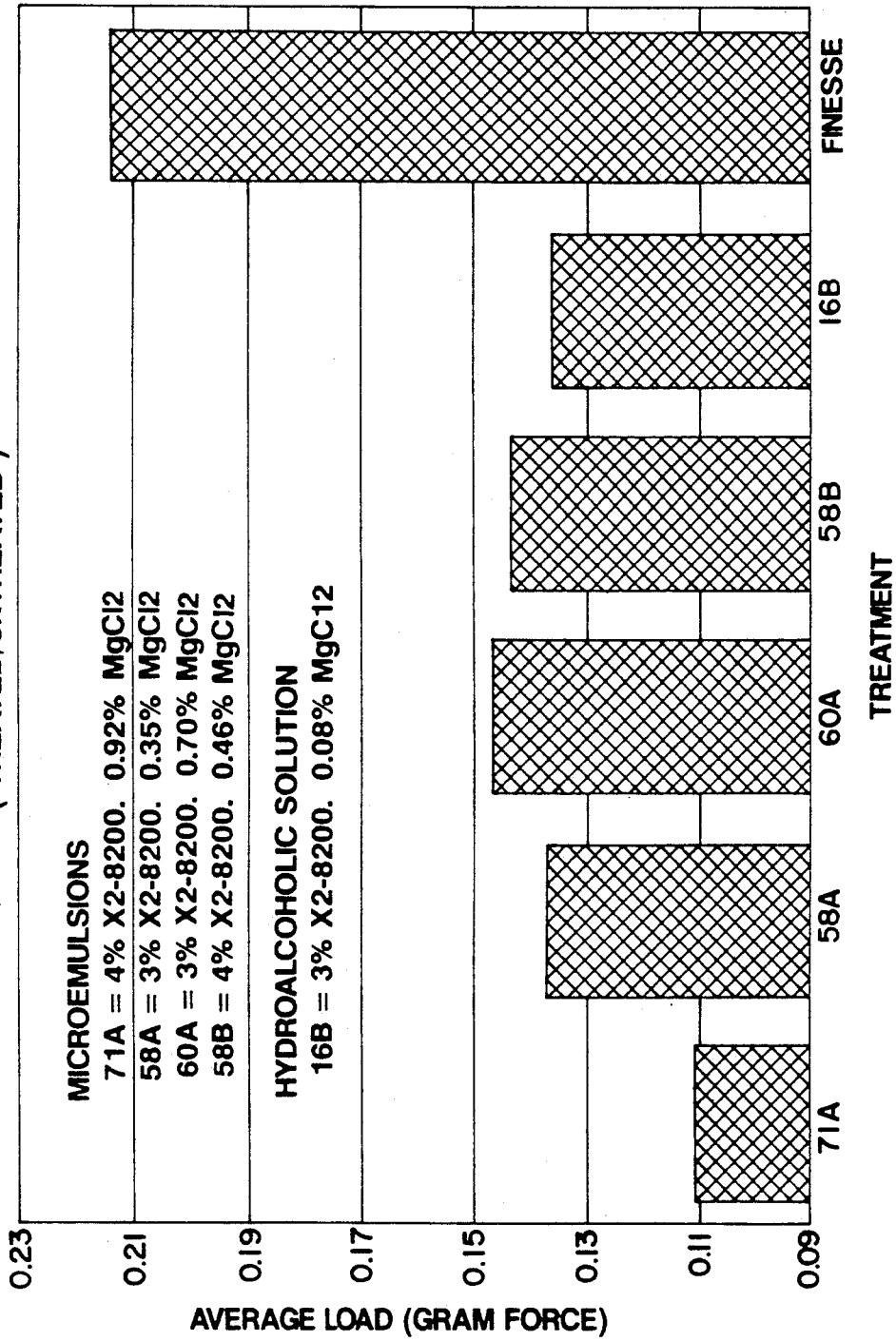
FIG. 1 is a bar graph comparing the wet combing index of hair treated with a microemulsion composition of the present invention (71A, 58A, 60A or 58B) to hair treated with either an alcohol-water solution of conditioning agents (16B) or the commercial conditioner FINESSE.

The microemulsion composition of the present invention comprises a water-insoluble amino-containing compound; an ionizable metal salt, wherein the metal has a valence of at least II; an ester compound having the general structural formula:

$$R_1-O-(A)_X-CH_2CO_2R_2.$$

wherein $R_1$ is an alkyl group including from about eight to about 18 carbon atoms, $R_2$ is an alkyl group including from one to about four carbon atoms, A is an alkylene oxide moiety wherein the alkylene group includes from one to about four carbon atoms, and X is a number in the range of from about 4 to about 20; and water; and having a pH of less than 7, and a particle size in the range of from about 0.1 nm (nanometers) to about 250 nm.

The water-insoluble amino-containing compound employed in the composition of the present invention can be a monomeric primary, secondary, or tertiary amine, having the structural formulas $R_3NH_2$, $R_3R_4NH$ and $R_3R_4R_5N$, respectively, wherein $R_3$, $R_4$ and $R_5$ can be the same or different alkyl or substituted alkyl moiety, or group, of sufficient carbon chain length or total carbon content to render the amine water-insoluble. The water-insoluble amino-containing compound also can be a diamine or a polymeric compound that contains either a primary or a secondary amino-functionality. In either case, the amino-containing compound contains at least one alkyl group, or substituted alkyl group, such as a silicon-containing alkyl group, of sufficient carbon chain length or total carbon content to render the amino-containing compound water insoluble. Therefore, as used here and hereinafter, the term water-insoluble amino-containing compound refers to amino-containing compounds that are completely water insoluble and to amino-containing compounds having a water-solubility of about 0.5 g or less of amino-containing compound per 100 ml of water.

It has been found that including the water-insoluble amino-containing compound in the microemulsion composition improves the conditioning properties of hair treated with the microemulsion composition. In addition, the conditioning properties are more durable and last through subsequent shampooings because the water-insoluble amino-containing compound apparently complexes to the hair through the metal ion, and therefore is not readily rinsed from the hair.

Generally, for a monomeric primary amine, a carbon chain length of at least five carbon atoms provides sufficient water-insolubility for the amine to impart improved conditioning and hair set properties to the hair when the amine is incorporated into a composition of the present invention. Similarly, for monomeric secondary and tertiary amines, as long as at least one alkyl or substituted alkyl group of the amine contains a carbon chain of at least five carbon atoms, or contains a sufficient number of carbon atoms in total, or contains a carbon and silicone chain of at least five carbon and silicone atoms in total, the monomeric secondary or tertiary amine is sufficiently water insoluble to be useful in the composition of the present invention.

Likewise, a water-insoluble diamine or polymer that contains a primary or a secondary amino-functionality can be used in place of, or in combination with, the water-insoluble, monomeric primary, secondary or tertiary amine, as long as the water solubility of the amino-containing polymer is about 0.5 g or less per 100 ml of water. For example, a water-insoluble ethoxylated amine having primary or secondary amino-groups can be used as the water-insoluble amino-containing compound in the composition of the present invention. An example of a diamine that can be used in the composition and method of the present invention is ADOGEN 572, N-stearyl-1,3-propanediamine, having the formula $C_{18}H_{37}NH(CH_2)_3NH_2$, and available from Sherex Chemical Co., Dublin, Ohio.

In addition, amino-functionalized silicones, such as trimethylsilylamodimethicone, as depicted in general structural formula I, are sufficiently water-insoluble to be useful in the composition of the present invention:

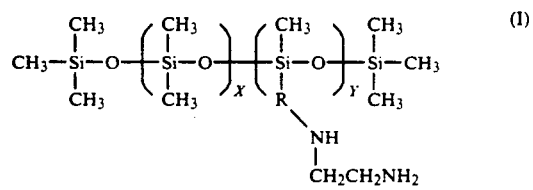

wherein $X+Y$ is a number from about 50 to about 500, and the mole % amine functionality is in the range of from about 0.7% to about 8%, and wherein R is an alkyl group having from 2 to 5 carbon atoms. Preferably, the number $X+Y$ is in the range of from about 100 to about 300, and the mole % amine functionality is in the range of from about 2% to about 6%. An example of an amino-functionalized silicone useful in a composition of the present invention is DOW CORNING X2-8200. Examples of other amino-functionalized silicones useful in the composition of the present invention include DOW CORNING X2-8107, Q2-8220, X2-8123, X2-8124, X2-8120, Softener CSF, and X2-8230, all available from Dow Corning Corp., Midland, Mich. Each of these amino-functionalized silicones was included in a microemulsion composition of the present invention and found to improve the conditioning properties of treated hair.

Furthermore, in order to ensure that the amino-functionalized silicone, or polymer containing primary or secondary amino-functionalities, is sufficiently water-insoluble, other hydrophilic functionalities, such as hydroxy, carbonyl, sulfhydryl and similar hydrophilic groups, should be absent from the amino-containing compound. It has been found that water-soluble quaternary ammonium salts and water-soluble amines, such as monoethanolamine and triethanolamine, do not provide the same degree of improved hair conditioning properties that are provided by a composition of the present invention including a water-insoluble amino-containing compound.

In addition to increasing the water solubility of the amino-containing compounds, hydrophilic functionalities, such as quaternary ammonium and carbonyl, also reduce the basicity of the amino-containing compounds by inductive and/or resonance effects thereby reducing the ability of the amino-containing compound to coordinate with the metal ions of the ionizable metal salt after application to the hair. Furthermore, because quaternary ammonium chlorides are substantive to the hair, the hair then is unavailable to coordinate with the metal ion of the ionizable metal salt included in the composition of the present invention.

Therefore, it has been found that particularly advantageous monomeric amines, amino-functionalized silicones or amino-group containing polymers have at least one amino functionality and at least one carbon, or carbon-silicon, chain of five atoms or longer. Examples of suitable amines, amino-containing silicones and amino-containing polymers include, but are not limited to, octylamine, dioctylamine, trioctylamine, dimethyloctylamine, trimethylsilylamodimethicone, water-insoluble polyethylenimines, pentylamine, dipentylamine, hexylamine, dihexylamine, trihexylamine, heptylamine, dodecylamine, hexadecylamine, octadecylamine, tallow amine, hydrogenated-tallow amine, di(-hydrogenated-tallow) amine, tri(hydrogenated-tallow) amine, dilaurylmethylamine, oleyl amine, soya amine, cocamine, dicocamine, methyl dicocamine, dimethylcocamine, dimethyldodecylamine, dimethyltetradecylamine, dimethylhexadecylamine, dimethyltallowamine, dimethyloleylamine, dimethylsoyamine, tridodecylamine, and methyl stearylamine; or mixtures thereof. Preferably, octylamine, pentylamine, dipentylamine, trimethylsilylamodimethicone, dioctylamine, trioctylamine, cocamine, hydrogenated- tallow amine, di(hydrogenated-tallow) amine, tri(hydrogenated-tallow) amine, or a water-insoluble ethoxylated amine; or mixtures thereof, are combined with the other essential ingredients to provide a microemulsion composition of the present invention. To achieve full advantage of the present invention, trimethylsilylamodimethicone is used as the water-insoluble amino-containing compound.

In addition, the amount of water-insoluble amino-containing compound included in the microemulsion composition is not particularly limited. However, the water-insoluble amino-containing compound usually is included in a composition of the present invention in an amount ranging from about 0.1% to about 6%, by weight of the composition. At concentrations above about 6% by weight no further improvements in hair conditioning are demonstrated, and the excess amount of water-insoluble amino-containing compound therefore is wasted. At concentrations below about 0.1% by weight of the composition, an appreciable improvement in hair conditioning properties is not observed. Preferably, the water-insoluble amino-containing compound is included in the composition in a range of from about 0.5% to about 4% by weight of the microemulsion composition.

As previously stated, the microemulsion composition of the present invention also includes an ionizable metal salt, wherein the metal has a valence of at least II. It has been demonstrated that combining a suitable ionizable metal salt with a water-insoluble amino-containing compound and an ester compound of general structural formula

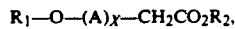

$R_1-O-(A)_x-CH_2CO_2R_2$.

provides a composition that, upon contacting human hair, surprisingly and unexpectedly improves the conditioning properties of the hair and imparts durable conditioning properties to the treated hair. It has been theorized that the metal salt complexes to the hair and to the amino-containing compound to deposit the amino-containing compound on the hair and therefore impart conditioning properties to treated hair. The metal salt fixes the amino-containing compound on the hair to help provide durable conditioning properties. As will be demonstrated more fully hereinafter, such durable conditioning properties are not observed if the metal ion is omitted from the composition. Furthermore, it is both surprising and unexpected for the microemulsion composition to demonstrate such excellent stability because the addition of a metal salt often destabilizes an emulsion and causes a phase separation. It also is surprising and unexpected for a composition of the present invention, that exhibits such excellent stability, to so effectively deposit the conditioning agents onto treated hair. Usually such stable compositions demonstrate poor deposition properties because the components of the stable composition are easily rinsed from the treated hair.

The ionizable metal salt utilized in the present invention is limited only in that the metal salt be capable of sufficient ionization in water, or therefore possesses a sufficient degree of water solubility; and in that the metal has a valence of at least II. It also should be understood, that in particular circumstances, a particular ionizable metal salt may or may not be suitable for use in the present invention because the inherent color of the ionizable metal salt may yield an esthetically unsuitable hair treating composition.

It has been found that an ionizable metal salt of metals having a valence of at least II can be used in the composition of the present invention, thereby precluding the use of the alkali metal salts. However, ionizable salts of the alkaline earth metals, such as magnesium, calcium and barium, have a valence of II and therefore are useful alone or in combination in the composition of the present invention. Similarly, ionizable salts of aluminum, titanium, vanadium, manganese, mercury, cadmium, lead, iron, cobalt, nickel, silver, copper, cerium, hafnium, germanium, zinc and zirconium, or combinations thereof, are suitable for use in the present invention. In addition, any other ionizable metal salt, wherein the metal has a valence of at least II, can be used alone or in combination with the above-mentioned metals.

The anion of the ionizable metal salt can be any anionic moiety, either organic or inorganic in chemical structure, that permits or facilitates ionization of the ionizable metal salt in aqueous solution. The principal importance of the anion is to control release of the metal cation through ionization, and therefore, the anion can be any of the halides, such as bromide or chloride; sulfate; nitrate; phosphate; acetate; lactate; or like organic or inorganic anions that easily dissociate and do not react with the hair or other composition components. As will be discussed more fully hereinafter, because the composition of the present invention is maintained at a pH of less than 7, anions such as hydroxyl, carbonate and bicarbonate may not be suitable as the anion of the ionizable metal salt.

Examples of ionizable metal salts of metals having a valence of at least two that have demonstrated an unexpected ability to impart improved and durable hair conditioning properties to hair include, but are not limited to, aluminum chloride, aluminum sulfate, aluminum lactate, calcium sulfate, cupric chloride, magnesium chloride, zinc chloride and ferric chloride. Furthermore, in order to achieve the full advantage of the present invention, it has been found that the molar quantity of the ionizable metal salt, or metal salts, utilized in the composition of the present invention should be equal to or greater than the molar, or molar-equivalent, quantity of the water-insoluble amino-containing compound used in the microemulsion composition.

The amount of the ionizable metal salt included in the microemulsion composition is limited only by the amount of metal salt that can be incorporated into the composition by solubilization or microemulsification, by the esthetics of the composition, and by the type of commercial product desired, such as a hair shampoo, hair conditioner, or hair lotion. In general, the ionizable metal salt is included in the microemulsion composition in an amount ranging from about 0.005% to about 4%, and preferably from about 0.01% to about 2%, by weight of the composition. To achieve the full advantage of the present invention, the molar amount of the metal salt should equal or exceed the molar or molar equivalent amount of the water-insoluble amino-containing compound in the microemulsion composition. An excess amount of the ionizable metal salt, or of the amino-containing compound, included in the microemulsion composition does not adversely affect the treated hair. However, the amount of amino-containing compound and ionizable metal salt that is substantive to the hair is finite, therefore an excess amount of amino-containing compound or metal salt is rinsed away during hair treatment and as a result is wasted.

In addition to the water-insoluble amino-containing compound and the ionizable metal salt, the composition of the present invention also includes an ester compound having the general structural formula (II):

$$R_1-O-(A)_X-CH_2CO_2R_2. \qquad (II)$$

wherein $R_1$ is an alkyl group or a substituted alkyl group including from about 8 to about 18 carbon atoms, $R_2$ is an alkyl group including from 1 to about 4 carbon atoms, A is an alkylene oxide moiety wherein the alkylene group includes from one to about four carbon atoms, and X is a number in the range of from about 4 to about 20. Preferred ester compounds having the general structural formula (II) include a straight-chain $R_1$ alkyl group having from about 10 about 16 carbon atoms, an $R_2$ alkyl group including two or three carbon atoms, A is oxylene oxide and X is in the range of from about 7 to about 15. An ester compound of general structural formula (II), when included in the microemulsion composition in an amount ranging from about 0.2% to about 15%, and preferably from about 2% to about 10%, by weight, provides a stable, microemulsion composition. An ester compound of general structural formula (II) present in the microemulsion composition in amounts greater than about 15% does not adversely affect the composition. However, at such high concentrations, the amount of ester compound exceeds the amount necessary to emulsify the other composition ingredients and therefore is wasted. The lower limit of the amount of ester compound included in the compound is determined by the amount of water-insoluble amino-containing compound included in the composition.

Surprisingly and unexpectedly, unlike prior art microemulsion compositions, a secondary emulsifier is not required, and the order of addition of composition ingredients does not affect the formation, or the stability, of the microemulsion composition of the present invention. A secondary emulsifier optionally can be included in the microemulsion composition, and accordingly a lower amount of the ester compound is included in the composition. However, microemulsion composition stability and performance are nevertheless maintained even if only the ester compound of general structural formula (II) is used or an emulsifier. In addition, the amount of the ester compound included in the composition is surprisingly low to form a stable microemulsion in comparison to the prior art teachings of using normally at least about 20% by weight of a primary emulsifier, and then, in addition, a secondary emulsifier.

A particular ester compound of general structural formula (II) useful in the composition of the present invention is isopropyl $C_{12-15}$ pareth-9 carboxylate, depicted by structural formula (III):

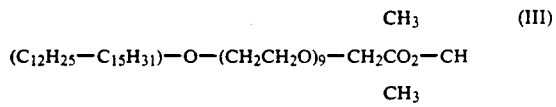

and commercially-available under the brandname VELSAN® P 8-3, from Sandoz Chemicals Corp., Charlotte, N.C. In general, it has been found that as the number of carbon atoms in the $R_1$ alkyl moiety increases, then the numeral X should be sufficiently large to provide an ester compound of general structural formula (II) having a calculated HLB (hydrophile-lipophile balance) value of from between about 10 to about 20, and preferably from about 15 to about 20. By using an ester compound having the correct balance between the hydrophile (i.e., the numeral X) and the lipophile (i.e., the $R_1$ alkyl moiety), an oil-in-water microemulsion composition having a particle size of from about 0.1 nm to about 250 nm is provided by simply thoroughly admixing the composition ingredients.

In further regard to the ester compound of general structural formula (II), it has been found that isopropyl $C_{12}-C_{15}$ pareth-9 carboxylate provided a stable, clear microemulsion, whereas cetyl $C_{12}-C_{15}$ pareth-9 carboxylate (VELSAN® P 8-16) did not. Accordingly, the $R_2$ group in the compound of general structural formula (II) should not include more than about four carbon atoms. Similarly, the compound isopropyl PPG-2-isodeceth-7 carboxylate (VELSAN® D8P-3) provided microemulsion compositions, but VELSAN® D8P-3 did not perform as well as VELSAN® P 8-3. Accordingly, it is preferred that, in ester compounds of general structural formula (II), A is ethoxy, $R_1$ is a linear, as opposed to a branched, alkyl moiety of at least ten carbon atoms and the compound has an HLB of about 15.

The ratio of the amount of ester compound of structural formula (II) to the amino-containing compound should be at least about 0.75 to 1 to provide a translucent or transparent microemulsion composition. It has been found that in a hair shampoo/conditioner formulation, including a relatively large amount of anionic surfactant, that the 0.75 to 1 ratio of ester compound to amino-containing compound is sufficient to provide a clear, esthetically-pleasing product. However, in a conditioner formulation, absent an anionic surfactant, it has been found useful to increase the ratio of ester compound to amino-containing compound up to from about 1.5:1 to about 2:1. In addition, an optional secondary emulsifier, like PEG-78 glyceryl monococoate, available commercially as VARONIC L167 from Sherex Chemical Company, Dublin, Ohio, or VELSAN® P 8-16 or VELSAN® D8P-3, can be added to the composition in addition to the ester compound of general structural formula (II). It has been found that including an optional secondary emulsifier is most useful when the amount of ester compound of general structural formula (II) is present in low amounts, such as less than about 3% by weight.

It also has been demonstrated that regardless of the percentage amount of the ionizable metal salt, the water-insoluble amino-containing compound and the ester compound of structural formula (II) included in the microemulsion composition, the composition should have a pH of less than 7, and preferably in the range of from about 3 to about 6.8, in order to provide a stable microemulsion composition that imparts improved and durable conditioning properties to treated hair. At pH values appreciably below 3, the hair itself can become protonated and therefore unavailable for treatment by the composition of the present invention. In addition, at pH values of 7 or greater, the stability of the composition is diminished, and separation or precipitation of composition ingredients can occur after a relatively short storage time. Furthermore, it has been found that regardless of the type of hair tested, such as virgin brown hair, 50% gray hair, bleached blond hair and permanent-wave hair, that microemulsion compositions having a pH at 7 or above did not provide the advantages and benefits of imparting improved conditioning properties to treated hair.

The microemulsion composition of the present invention preferably is adjusted to a suitable pH range with an appropriate buffer. The buffering capability of the composition may be important because the pH of the composition on the hair should be maintained at less than 7, and preferably between 3 and 6.8. Therefore, appropriate buffers include citric acid, phosphoric acid, phthalic acid, or mixtures thereof, in addition to other organic or inorganic and other buffers well-known in the art. However, the pH of the composition also can be adjusted with well-known mineral and organic acids that do not possess a buffering capacity, such as hydrochloric acid.

Water also is an essential ingredient in the microemulsion composition of the present invention. The water is present in an amount of at least about 65% by weight of the composition, and usually in an amount of at least 75% by weight of the composition. The amount of water in the composition ultimately is determined by the amount of the other essential and optional ingredients included in microemulsion composition.

Other common cosmetic additives also can be incorporated with the essential ingredients of the present invention, as long as the basic properties of the microemulsion composition are not adversely affected. In general, it has been found that as long as the additive is soluble in the continuous phase, it can be included in the microemulsion composition of the present invention. These additives include, but are not limited to, commonly used fragrances, dyes, opacifiers, pearlescing agents, conditioning agents, cleansing surfactants, foam stabilizers, viscosity adjusting agents, preservatives, water softening agents and the like; and will usually be present in weight percentages of less than about 1% each, and about 2% to about 5% in total. Cleansing surfactants, if present, usually are present in weight percentages up to about 25% active basis by weight of the composition, and usually from about 10% to about 20% active basis by weight of the composition. Sequestering agents should be avoided to preclude a complexing interaction between the metal ion and sequestering agent, thereby making the metal ion unavailable to treat hair.

As discussed above, the microemulsion composition vehicle is predominantly water, but organic solvents also can be added to the composition in order to solubilize compounds that are not sufficiently soluble in water. Suitable solvents include those that do not react with the ionizable metal salt or the amino-containing compound such as the lower alcohols like ethanol and isopropanol; polyols like glycerol; glycols or glycol ethers, like 2-butoxyethanol, ethylene glycol, ethylene glycol monoethyl ether, propylene glycol and diethylene glycol monomethyl ether; and mixtures thereof. These solvents can be present in the microemulsion composition of the present invention in an amount from about 0% to about 50% by weight, and in particular from about 0.5% to about 25% by weight, of the total weight of the composition.

The microemulsion compositions can be thickened, for example, with sodium alginate; gum arabic; cellulose derivatives, such as methylcellulose, hydroxyethylcellulose, hydroxypropylmethycellulose and carboxymethylcellulose; and various polymeric thickeners, such as acrylic acid derivatives; sodium methyl cocoyl taurate, dimethicone copolyol, polyethylene glycol distearates and polyethylene glycol methyl glucose dioleates. Inorganic thickeners such as bentonite also can be used. These thickeners are present in an amount ranging from about 0.1% to about 10% by weight, and in particular from about 0.3% to about 3% by weight, relative to the total weight of the composition.

The microemulsion compositions of the present invention can be formulated into a hair conditioning product, absent cleansing surfactants, or can be formulated into hair shampoo/conditioner composition including anionic, amphoteric or nonionic surfactants, or a combination thereof, to impart cleansing properties to the composition. Likewise, the compositions can contain other emulsifiers, fatty alcohols, humectants, conditioning agents and similar materials, such as cetyl alcohol, stearyl alcohol, a dimethicone, a cyclomethicone or a phenyl dimethicone, to provide further improved conditioning properties, esthetic properties and desirable physical properties to the composition.

For example, representative nonionic surfactants include esters of polyols and sugars; the polyethoxylated and/or polypropoxylated alkylphenols; the polyhydroxylated polyethers of fatty alcohols; alkanolamides; and the condensation products of ethylene oxide with long chain mercaptans or long chain amides. Similarly, representative anionic surfactants include alkali metal salts, ammonium salts or salts of amines or aminoalcohols of fatty acids such as oleic acid; of the sulfates of fatty alcohols, principally $C_{12-14}$ and $C_{16}$ fatty alcohols; of the sulfates of polyethoxylated fatty alcohols; the alkylbenzenesulfonates, such as those wherein the alkyl moiety has 12 carbon atoms; or the alkylarylpolyether sulfates and monoglyceride sulfates.

More particularly, typical cleansing surfactants include anionic surfactants such as the magnesium, sodium, ammonium, potassium or triethanolamine salts of lauryl sulfate and lauryl ether sulfate; nonionic surfactants such as fatty acid alkanolamides like lauric acid diethanolamide (lauramide DEA), lauramide MEA, cocamide DEA, cocamide MEA, capramide DEA, ricinoleamide DEA, soyamide DEA, myristamide DEA, stearamide DEA, oleylamide DEA, tallowamide DEA, lauramide MIPA, stearamide MEA, tallowamide MEA, isostearamide MEA, isostearamide DEA, myristamide MEA or combinations thereof; and amphoteric surfactants such as N-cocamidopropyl dimethyl glycine. The anionic surfactants, such as the sodium, magnesium, ammonium, potassium and triethanolamine salts of lauryl sulfate, are preferred because they provide richer and more stable foam than other cleansing surfactants at comparable concentrations. All these nonionic, amphoteric and anionic surfactants, as well as numerous others not cited herein, are well known in the art and are fully described in the literature. Many additional anionic, nonionic and amphoteric surfactants are described in McCUTCHEON'S DETERGENTS AND EMULSIFIERS, 1989 ANNUAL, published by McCutcheon Division, MC Publishing Co., and herein incorporated by reference.

In another embodiment of the present invention, the microemulsion composition is a conditioner, or a conditioning shampoo, that includes an additional conditioning agent, like a fatty alcohol or a volatile or a nonvolatile silicone or hydrocarbon. In addition, the microemulsion composition of the present invention can be formulated as a hair spray, hair gel, aerosol hair mousse or other hair care or styling product designed to condition or impart hair conditioning properties to the treated hair. Furthermore, the microemulsion composition can be a product designed to fix the hair into a particular hair style. Usually, a hair fixing technique includes the application of a composition including a polymeric agent to coat the hair. After coating the hair, the polymeric agent dries and stiffens on the hair shaft to fix the hair in the desired hair style. These hair fixative products often leave the hair in a poor cosmetic state. Accordingly, it has been found that incorporating a hair fixative compound, including a polymeric compound like polyvinylpyrrolidone, sodium polystryrenesulfonate, copolymers of vinylpyrrolidone and methacrylic acid, vinylpyrrolidone and vinyl acetate, vinyl methyl ether and vinylpyrrolidone, vinyl methyl ether and maleic acid, and vinylpyrrolidone and dimethylaminoethylmethacrylate and other well-known water-soluble polymeric compounds, into a microemulsion composition of the present invention conditions the hair, and thereby provides hair having a desired hair style with good physical and esthetic properties. In general, the hair fixative compound is included in the microemulsion composition in amounts up to about 5% by weight of the composition.

The microemulsion composition of the present invention also can be included in an aerosol mousse product to impart durable conditioning properties to the hair. For example, it has been found that a mousse product, including 90% by weight of a microemulsion composition of the present invention and 10% of a suitable propellant, such as a hydrocarbon, like butane, propane and combinations thereof; chlorofluorocarbons; dimethyl ether; and combinations thereof, imparted excellent conditioning properties to the hair, like dry combining, feel, luster and body.

In accordance with an important feature of the present invention, several microemulsion compositions were prepared, then applied to human hair to demonstrate the improved conditioning properties imparted by microemulsion compositions including a water-insoluble amino-containing compound; an ionizable metal salt, wherein the metal has a valence of at least II; an ester compound of structural formula (II); and water, having a pH of less than 7, and preferably from about 3 to about 6.8, and a particle size in the range of from about 0.1 nm to about 250 nm, and usually less than about 100 nm. Representative compositions, and their method of manufacture, are presented in the following Examples 1 through 5, showing that a microemulsion composition of the present invention can be formulated into a variety of end use products depending upon consumer preferences. In accordance with an important feature of the present invention, it should be understood that utilizing the correct amounts and proportions of the ester compound of structural formula (II), the water-insoluble amino-containing compound and metal salt provide a translucent or transparent microemulsion composition regardless of the formation of premixes including two or more of the composition ingredients. Accordingly, the methods of manufacture illustrated in Examples 1 through 5 are exemplary rather than limiting.

EXAMPLE I

Solution/Spray Formulation

| Ingredient | Wt % |
| --- | --- |
| 1. Water, deionized | q.s. to 100% |
| 2. Isopropyl $C_{12-15}$ Pareth-9 Carboxylate (VELSAN P 8-3) | 7% |
| 3. Trimethylsilylamodimethicone | 3% |
| 4. Magnesium Chloride Hexahydrate | 0.35% |
| 5. Hydrochloric Acid (HCl) | q.s. to pH 3-4.5 |
| 6. Preservatives, dyes, fragrances, and other optional components | as desired |

The amino-functionalized silicone, i.e. trimethylsilylamodimethicone, and the isopropyl $C_{12-15}$ pareth-9 carboxylate first are admixed, and then thoroughly blended to form a first mixture. This first mixture is added to the water, and the resulting mixture is admixed thoroughly. The magnesium chloride then is added to the mixture, and the resulting mixture is thoroughly blended. The pH of the spontaneously-formed microemulsion composition then is adjusted to between 3 and 4.5 with hydrochloric acid. Finally, any desired optional ingredients, such as preservatives, dyes and fragrances, are added to produce a clear microemulsion composition. The microemulsion composition is resistant to phase transitions in that an observed, elevated temperature phase transition is reversible, as demonstrated by the return of the composition to a clear microemulsion upon returning to ambient temperature.

As discussed previously, and as will be demonstrated more fully hereinafter, the amino-functionalized silicone can be interchanged with another water-insoluble amino-containing compound or compounds, and the magnesium chloride can be interchanged with another suitable ionizable metal salt or ionizable metal salts. For example, microemulsion compositions similar to the microemulsion compositions of EX. 1 were prepared that include dodecylamine, dilaurymethylamine or N-stearyl-1,3-propanediamine as replacements for the trimethylsilylamodimethicone. In addition, microemulsion compositions were prepared that substituted a calcium ion, a zinc ion, or an aluminum ion for the magnesium ion used in the microemulsion composition of EX. 1. Each of these microemulsion compositions was transparent or translucent, and demonstrated a thermal stability essentially identical to the microemulsion composition of EX. 1.

EXAMPLE 2

| Conditioner Formulation (Traditional-Type) | |
| --- | --- |
| Ingredient | Wt. % |
| 1. Water, deionized | q.s. to 100% |
| 2. Magnesium Chloride | 0.46% |
| 3. Glyceryl Monostearate | 1.5% |
| 4. Cetyl Alcohol | 1.0% |
| 5. Stearyl Alcohol | 1.0% |
| 6. Isopropyl $C_{12-15}$ Pareth-9 Carboxylate | 4.0% |
| 7. Trimethylsilylamodimethicone | 4.0% |
| 8. Hydrochloric Acid (HCl) | q.s. to pH 3.5 to 6 |
| 9. Preservatives, dyes, fragrances and other optional ingredients | as desired |

The water and magnesium chloride are admixed and heated to approximately 70° C. to 75° C. Then the glyceryl monostearate, cetyl alcohol and stearyl alcohol are admixed and heated to approximately 70° C. to 75° C. The water/metal salt mixture and the monostearate/alcohol mixture then are combined, and the resulting mixture is allowed to cool. Then, a premix including the isopropyl $C_{12-15}$ pareth-9 carboxylate and the trimethylsilylamodimethicone is added to the cooled mixture. Mixing is continued until the mixture is homogeneous and the temperature cools to ambient temperature. Then, the pH is adjusted to within the range of about 3.5 to 6 with hydrochloric acid. The optional ingredients then are added as desired. The final pH is adjusted to within in range of about 3.5 to about 6 to yield an opaque, thick end product. Although the composition has the appearance of a traditional macroemulsion, the composition is actually a microemulsion. The compounds glyceryl monostearate, cetyl alcohol and stearyl alcohol impart an opaque appearance to the composition to satisfy consumers preferring the traditional opaque appearance of a hair conditioner.

The composition of Example 3 is a transparent microemulsion conditioner of the present invention. In this Example, the optional ingredients glyceryl monostearate, cetyl alcohol and steary alcohol are omitted, and the optional ingredients included in the composition are water soluble. Therefore the composition of Example 3 is transparent. However, it should be understood that both the compositions of Example 2 and Example 3 are microemulsion compositions of the present invention.

EXAMPLE 3

| Conditioner Formulation (Transparent-type) | |
| --- | --- |
| Ingredient | Wt % |
| 1. Water, deionized | q.s. to 100% |
| 2. PEG-150 Distearate | 1.5% |
| 3. PEG-120 Methyl Glucose Dioleate | 1.5% |
| 4. PEG-78 Glyceryl Monococoate | 1.0% |
| 5. Isopropyl $C_{12-15}$ Pareth-9 Carboxylate | 3.0% |
| 6. Trimethylsilylamodimethicone | 4.0% |
| 7. Magnesium Chloride Hexahydrate | 0.46% |
| 8. Hydrochloric Acid (HCl) | q.s. to pH 3.5-6 |
| 9. Preservatives, dyes, fragrances and other optional ingredients | as desired |

The deionized water, PEG-150 distearate, PEG-120 methyl glucose dioleate and PEG-78 glyceryl monococoate were premixed and heated to approximately 55° C. to 60° C. After blending the premix until homogeneous, the homogeneous mixture was allowed to begin cooling. The isopropyl $C_{12-15}$ pareth-9 carboxylate and trimethylsilylamodimethicone also were premixed, then added to the aqueous homogeneous mixture. The resulting mixture was thoroughly stirred until homogeneous, then the magnesium chloride was added, followed by adjusting the pH to 3.5 to 6 with hydrochloric acid and the addition of any desired optional ingredients. After mixing until homogeneous and cooling to ambient temperature, the resulting composition was a thick, translucent liquid, suitable for use as a hair conditioner.

Analogous to the formulation presented in Example 1, the water-insoluble amino-containing compound and the ionizable metal salt used in EXS. 2 and 3 can be interchanged with other suitable insoluble amino-containing compounds and other suitable ionizable metal salts. Likewise, the cetyl alcohol, glyceryl monostearate, PEG-150 distearate and other optional ingredients included in EXS. 2 and 3 can be replaced with other fatty alcohols and conditioners as are well-known and practiced in the art of hair conditioner formulation. The microemulsion compositions of Examples 2 and 3 also are stable to elevated temperature phase transitions.

EXAMPLE 4

| Conditioning-Shampoo Formulation | |
| --- | --- |
| Ingredient | Wt % |
| 1. Water, deionized | q.s. to 100% |
| 2. Isopropyl $C_{12-15}$ Pareth-9 Carboxylate | 1.0% |
| 3. Sodium Lauryl Ether Sulfate (28% active) | 30.0% |
| 4. Lauramide DEA | 3.0% |
| 5. Octylamine | 1.0% |
| 6. PEG-120 Methyl Glucose Dioleate | 1.0% |
| 7. Zinc Chloride | 1.06% |
| 8. Hydrochloric Acid (HCl) | q.s. to pH 4.5-6.0 |
| 9. Preservatives, dyes, fragrances and other optional ingredients | as desired |

The sodium lauryl ether sulfate, lauramide DEA and PEG-120 methyl glucose dioleate are added to the water, and the resulting aqueous mixture heated to approximately 5° C. above the melting point of the lauramide DEA. The isopropyl $C_{12-15}$ pareth-9 carboxylate and octylamine are premixed, and then added to the aqueous mixture. The blend then is mixed until homogeneous. After adjusting the pH to within a range of about 4.5 to about 6.0 with hydrochloric acid, the metal salt and other optional ingredients are added to the homogeneous blend, and the resulting mixture is mixed to form a microemulsion. The final pH is adjusted to within the range of about 4.5 to about 6.0 with hydrochloric acid. A thick, clear shampoo, possessing good foaming properties, results.

EXAMPLE 5

| Clear Conditioning-Shampoo Formulation | |
| --- | --- |
| Ingredient | Wt % |
| 1. Water, deionized | q.s. to 100% |
| 2. Sodium Lauryl Ether Sulfate (30% active) | 50.0% |
| 3. Lauramide DEA | 3.0% |
| 4. Isopropyl $C_{12-15}$ Pareth-9 Carboxylate | 4.0% |
| 5. Trimethylsilylamodimethicone | 4.0% |
| 6. PEG-120 Methyl Glucose Dioleate | 1.5% |

| Clear Conditioning-Shampoo Formulation | |
|---|---|
| Ingredient | Wt % |
| 7. PEG-150 Distearate | 1.5% |
| 8. Magnesium Chloride Hexahydrate | 0.46% |
| 9. Hydrochloric acid (HCl) | q.s. to pH-4.5 |
| 10. Preservatives, dyes, fragrances and other optional ingredients | as desired |

The sodium lauryl sulfate, lauramide DEA, PEG-120 methyl glucose dioleate and PEG-150 distearate were added to the water. The resulting mixture was stirred and heated at approximately 60° C. until the mixture was homogeneous. The homogeneous mixture was allowed to begin cooling. Then, a premix of the isopropyl $C_{12}$-$C_{15}$ pareth-9 carboxylate and trimethylsilylamodimethicone was added to the cooling homogeneous mixture. After the premix was thoroughly blended into the homogeneous mixture, the magnesium chloride and other optional ingredients were added to form the microemulsion, and the pH of the composition was adjusted to about 4.5 with hydrochloric acid. A viscous, clear shampoo resulted.

As discussed previously in Examples 1 through 3, the water-insoluble amino-containing compound and the ionizable metal salt in Examples 4 and 5 can be interchanged with other suitable water-insoluble amino-containing compounds and other suitable ionizable metal salts. Likewise, the sodium lauryl ether sulfate, sodium lauryl sulfate lauramide DEA, PEG-120 methyl glucose dioleate and PEG-150 distearate can be replaced with other surfactants, detergents, amides, thickeners as are well known and practiced in the art of hair shampoo formulation, such as ammonium lauryl sulfate, glyceryl stearate, stearyl alcohol, capramide DEA, sodium methyl cocoyl taurate, ethylene oxide/propylene oxide block copolymers and polyethylene glycol (PEG) 6000 distearate.

To demonstrate the new and unexpected results achieved by the method and composition of the present invention, spray-type conditioners, pour-on-type conditioners and conditioning-shampoo products, as illustrated in Examples 1 through 5, were prepared, then applied to human hair. The treated hair then was tested to determine the ability of the microemulsion composition to condition the hair. It was found that the compositions of the present invention imparted excellent conditioning properties, such as wet combing, dry combing and sheen, to treated hair. In particular, the treated hair was tested by at least one of the following techniques to determine composition performance:

a) Instron combing that measures that energy required to comb through a hair tress to compare the energy required to comb through an untreated tress to the energy required to comb through a tress treated with a microemulsion composition;

b) Fourier transforms infrared spectroscopy (FTIR) that provides a quantitative determination of the amount of silicone conditioning compounds deposited on the hair;

c) Energy dispersive X-ray (EDX) that provides a qualitative or semiquantitative determination of the amount of conditioning agents deposited on the hair;

d) Salon half-head test that subjectively, but directly, compares two hair-treating compositions on a semiquantitative basis; and e) Panelist combing that utilizes trained human judges to rate various products for the ability to impart wet combing and dry combing conditioning properties to hair treated with the microemulsion composition of the present invention.

As will be discussed more fully hereinafter, these performance tests were used singly, or in combination, to evaluate the performance of the microemulsion compositions of the present invention. Accordingly, performance tests showed the ability of a microemulsion composition of the present invention to impart durable conditioning properties to the hair.

In general, the various hair treating compositions were tested by applying about one milliliter, or about one gram, of the composition to clean, wet, naturally dark brown tresses of normal virgin human hair, available commercially from DeMeo Brothers, New York, N.Y. The six inch hair tresses, each weighing two grams, were attached to a plastic tab at the root end. In each test, the composition was combed through the hair and allowed to contact the hair form from 15 seconds to 2 minutes. The hair was rinsed with 32° C. tap water for 30 seconds. Performance tests were conducted on either a wet treated tress or a treated tress dried with a blow dryer, as required by the particular performance test.

Accordingly, the following microemulsion compositions of Examples 6 through 9 labelled as 71A, 58A, 60A and 58B, respectively, in the FIGS. were prepared by simply admixing the ingredients in the order listed, with stirring, to provide a stable microemulsion composition. The four microemulsion compositions each were found to improve the conditioning properties of the treated hair. In particular, EXS. 6 through 9 demonstrate the effect of varying the amounts of amino-functionalized silicone and metal salt in the microemulsion composition.

| | MICROEMULSION COMPOSITIONS | | | |
|---|---|---|---|---|
| Ingredient | EX. 6 (71A) | EX. 7 (58A) | EX. 8 (60A) | EX. 9 (58B) |
| Water | q.s. to 100% | q.s. to 100% | q.s. to 100% | q.s. to 100% |
| Isopropyl $C_{12-15}$ Pareth-9 Carboxylate 1) | 7% | 7% | 7% | 7% |
| Trimethylsilyl-amodimethicone 2) | 4% | 3% | 3% | 4% |
| Magnesium Chloride Hexahydrate | 0.92% | 0.35% | 0.70% | 0.46% |
| Hydrochloric Acid (1M) | q.s. to pH 7 | q.s. to pH 7 | q.s. to pH 7 | q.s. to pH 7 |

1) VELSAN ® P 8-3, Sandoz Chem. Corp., Charlotte, N.C.
2) X2-8200, Dow Corning Corp., Midland, MI.

For example, FIG. 1 illustrates the performance results obtained for the Instron combing test on wet tresses treated by the four microemulsion compositions 71A, 58A, 60A and 58B of EXS. 6-9, respectively; a 50% water-50% isopropyl alcohol solution of magnesium chloride (0.08%) and trimethylsilylamodimethicone (3%), and labelled as 16B; and FINESSE, a premium, commercial hair conditioner available from Helene Curtis, Inc., Chicago, Ill. The Instron combing test measured the force needed to comb through a wet, treated hair tress. First, an untreated, wet hair tress is tested and assigned an index value of one. Then a treated wet hair tress is tested, and if the treated hair tress exhibits an index value of less than one, then less energy is required to comb through the treated tress than the untreated tress. Therefore, the lower the index value, the easier it is to comb the hair, i.e. the hair is more conditioned.

Accordingly, the bar graph in FIG. 1 shows that FINESSE, recognized in the industry as a premium hair conditioner, demonstrated a wet combing index of about 0.21. However, the four compositions of the present invention, 71A, 58A, 60A, and 58B, each demonstrated a substantially improved wet combing index of from about 0.11 to about 0.15 over untreated hair and over FINESSE; and each composition essentially equalled the known exceptional conditioning properties imparted by the alcohol-water solution of conditioning compounds (16B). It should be understood that composition 16B is not as stable as the microemulsions of the present invention because the conditioning compounds do not remain in solution when water, such as rinse water, contacts the composition. In contrast, the conditioning compounds included in the microemulsion composition of the present invention remain in solution upon the addition of water. Accordingly, it is expected that composition 16B should deposit the conditioning compounds on the hair more effectively than a composition of the present invention. Surprisingly, the stable microemulsion compositions demonstrated an essentially equal ability to deposit the conditioning agents on the hair as the less stable hydroalcoholic composition 16B.

Overall, the microemulsion compositions of the present invention demonstrated better wet combing properties than FINESSE, a premium, commercial macroemulsion composition; and equal wet combing properties to a less stable composition including the same conditioning agents as the microemulsion compositions. Therefore, the conditioning agents present in the microemulsion composition are deposited on the hair shaft as effectively as the identical conditioning agents present in a less stable, macroemulsion composition.

Figure 2:
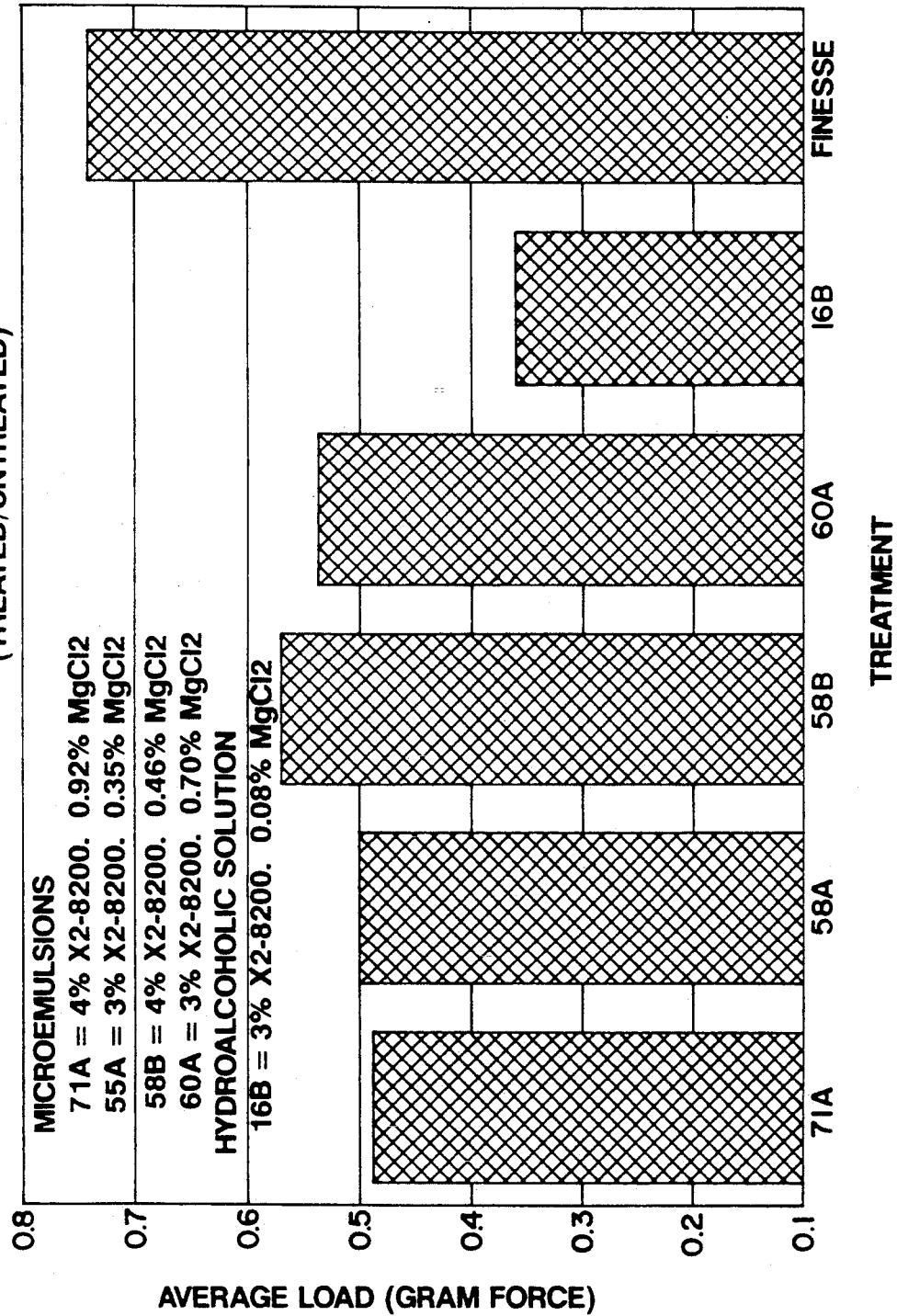
FIG. 2 is a bar graph comparing the dry combing index of hair treated with a microemulsion composition of the present invention (71A, 58A, 60A or 58B) to hair treated with either an alcohol-water solution of conditioning agents (16B) or the commercial conditioner FINESSE.

FIG. 2 demonstrates similar results for the dry combing Instron combing test. The four microemulsion compositions of EXS. 6-9, i.e. 71A, 58A, 60A and 58B, were compared to FINESSE and a 50/50 isopropyl alcohol-water solution of conditioning agents (16B). Again, each of the microemulsions outperformed FINESSE, i.e. a dry combing index ranging from about 0.5 to about 0.57 for the microemulsion compositions compared to about 0.73 FINESSE; and each of the microemulsions approached the performance of the relatively unstable alcohol-water composition. As previously discussed, it is expected that a less stable composition (16B) would deposit more conditioning agents on the hair, and therefore impart more improved conditioning properties to the hair. However, it nevertheless is surprising that the stable microemulsions of the present invention deposited sufficient conditioning agents on the hair to essentially equal the performance of composition 16B and to outperform FINESSE.

In regard to the microemulsion compositions 71A, 55A, 60A and 58B in EXS. 6 through 9, it should be noted that compositions 71A and 58B each include 4% trimethylsilylamodimethicone, however composition 71A includes 0.92% magnesium chloride, for a 2 to 1 molar ratio of metal ion to amino-containing compound, and composition 58B includes 0.46% magnesium chloride, for a 1 to 1 molar ratio of metal ion to amino-containing compound. Similarly, compositions 58A and 60A each include 3% trimethylsilylamodimethicone, with composition 60A having a 2 to 1 molar ratio of metal ion to amino-containing compound (0.70% magnesium chloride) and composition 58A having a 1 to 1 molar ratio of metal ion to amino-containing compound. The results presented in FIGS. 1 and 2 show that these differences in ingredients percentages and ratios did not significantly affect a microemulsion composition performance.

Figure 3:
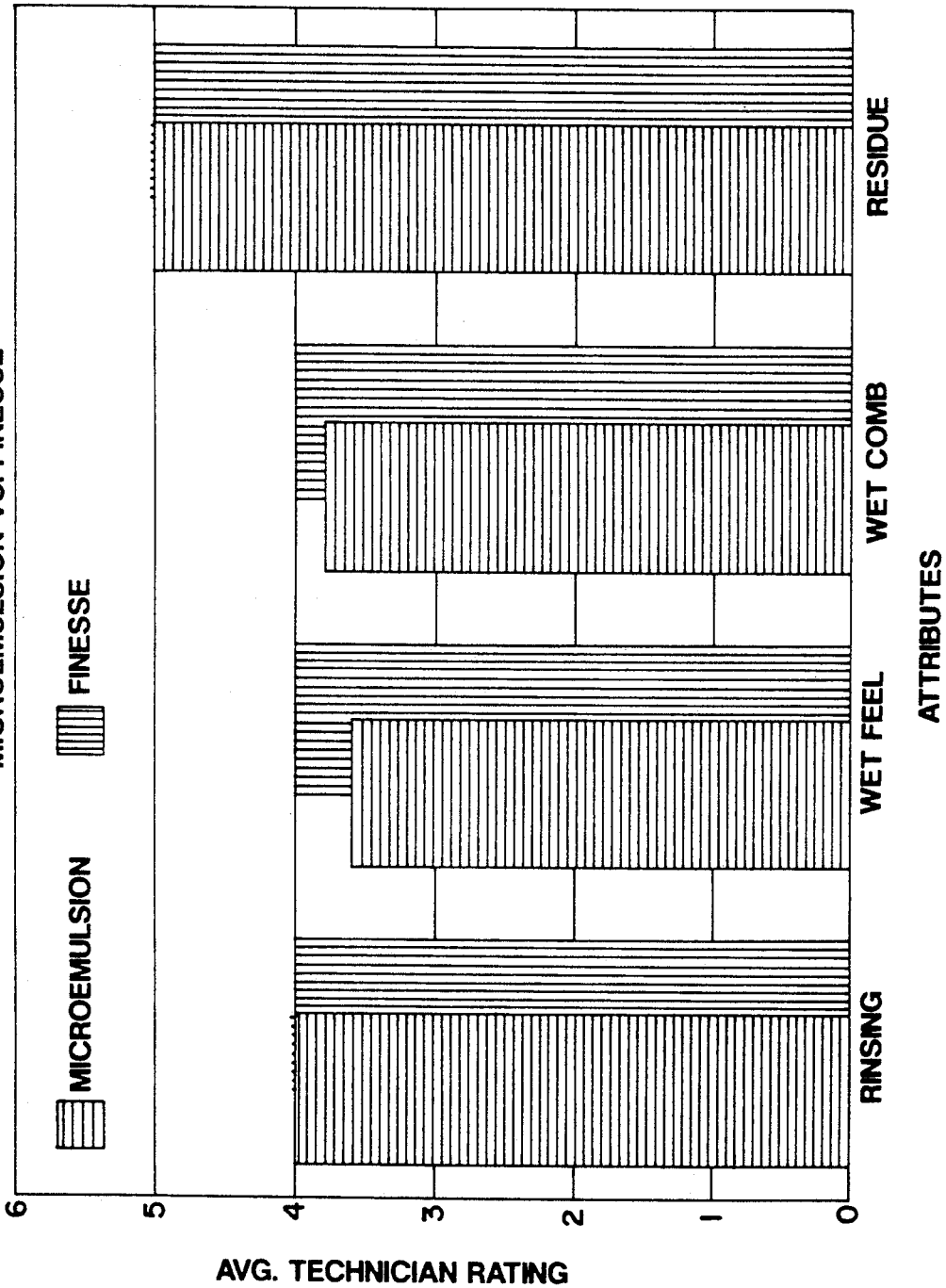
FIG. 3 through 5 are bar graphs comparing the conditioning properties imparted to hair treated with a microemulsion composition of the present invention and the conditioning properties imparted to hair treated with FINESSE.
Figure 4:
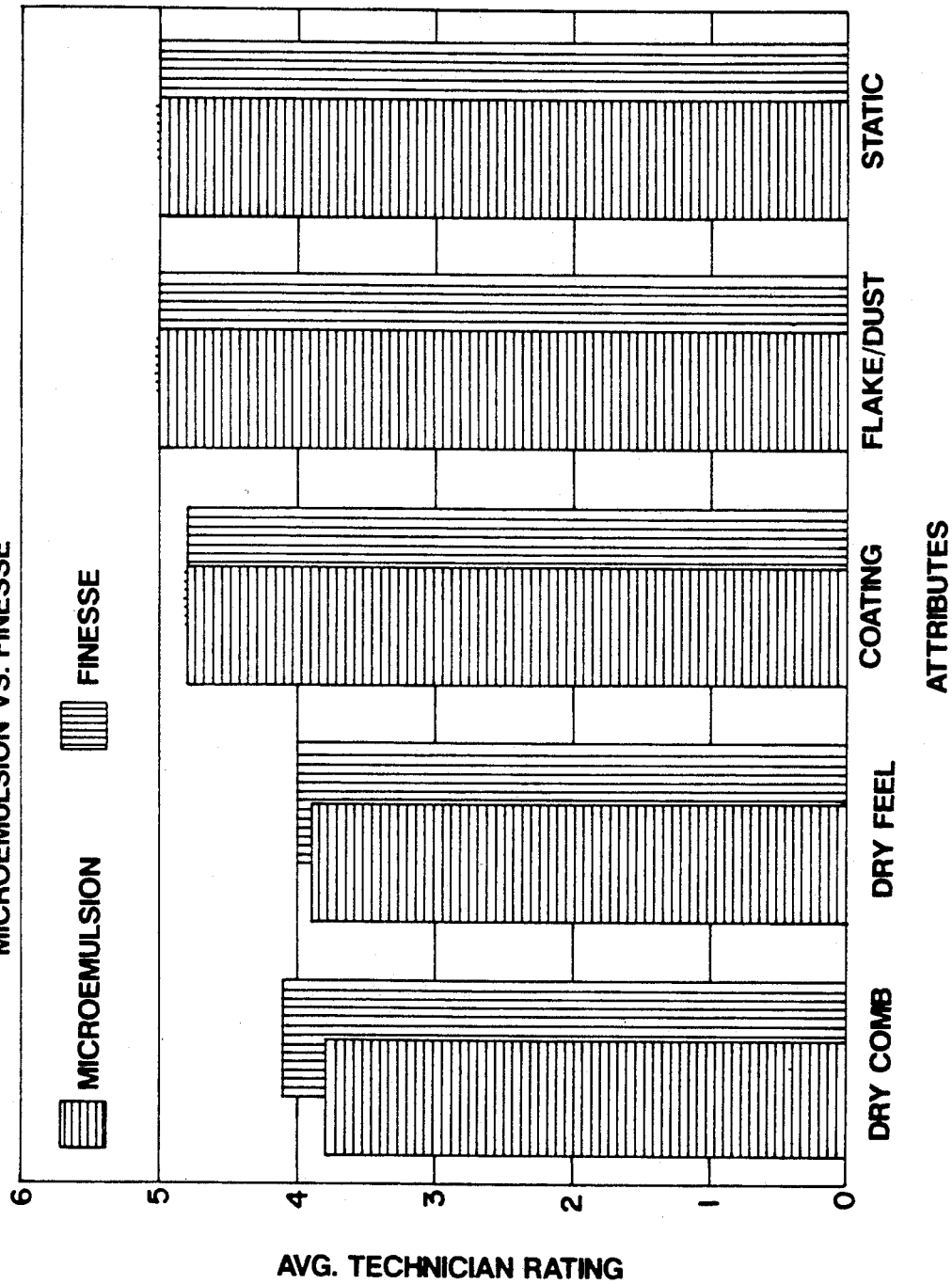
Figure 5:
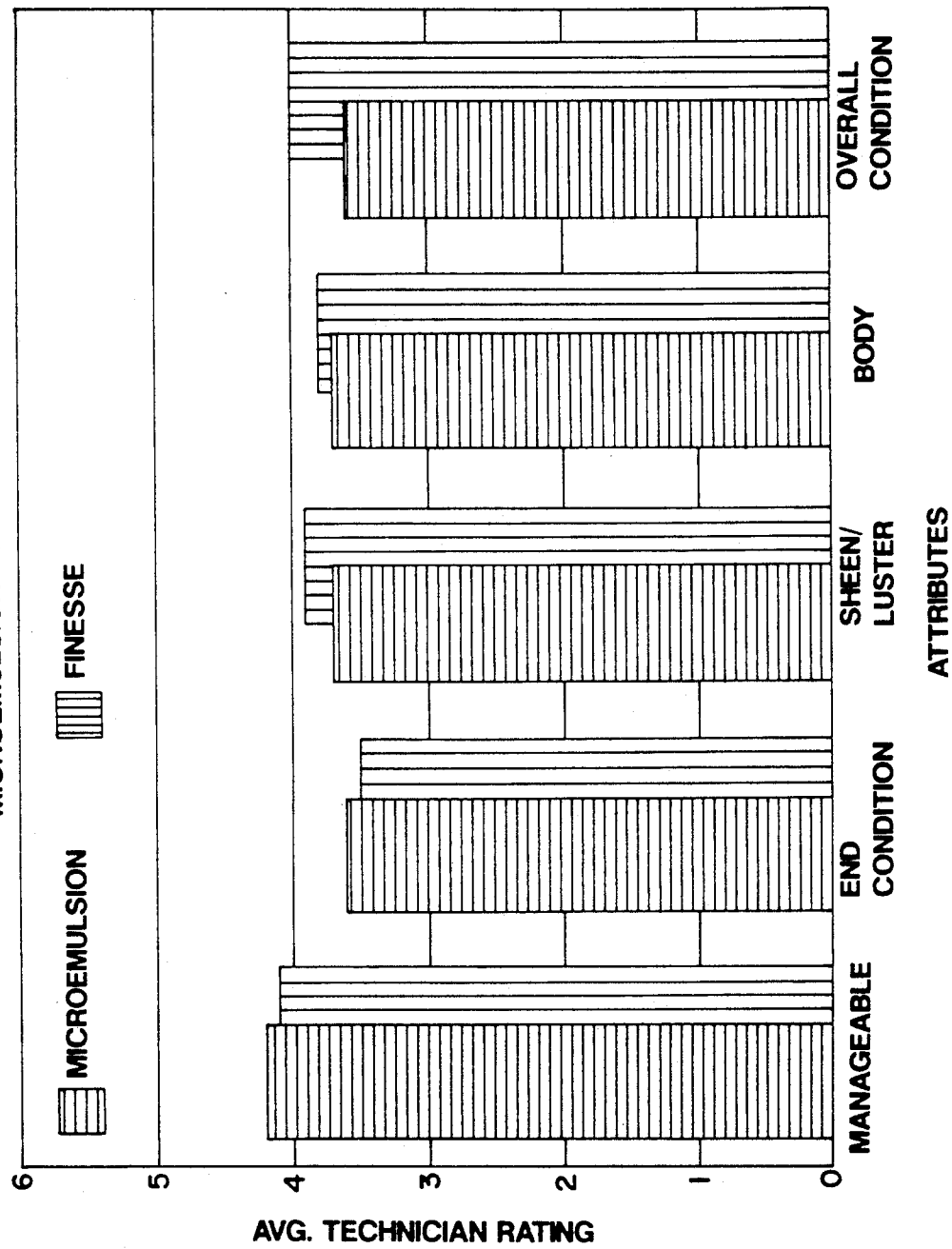

FIGS. 3 through 5 summarize the results of a half-head salon test comparing the microemulsion composition 58B of EX. 9 to FINESSE. In a half-head test, the composition of interest is applied to one side of a head of hair, and the product used for comparison, i.e., FINESSE, is applied to the other side of the head. After the treatment, each side of hair is judged for a variety of hair conditioning properties by a trained judge on a ranking of 1 unit (worst) to 5 units (best). Five different heads of hair are so treated, and each head of hair is evaluated by a trained judge. Then ratings of the judges for each hair conditioning property are averaged, and a difference in rating one side of hair compared to the other side of hair of at least 0.3 units is considered a significant difference for that particular hair conditioning property. The judges rate the hair for such hair conditioning properties as ease of application, fragrance, ease of rinsing, wet feel, wet comb, residue, dry combing, dry feel, coating, flakes/dust, static, manageability, condition of ends, sheen/luster, body, effect on hair color, irritation and overall condition. It should be noted that in this subjective salon testing, if a composition imparts hair conditioning properties to treated hair equivalent to the properties imparted by FINESSE, the composition is considered an exceptional conditioner because FINESSE is recognized as a benchmark for hair conditioning performance.

Accordingly, the microemulsion composition 58B of the present invention was compared to the FINESSE conditioner for fourteen particular hair conditioning properties. FIGS. 3 through 5 illustrate that the hair conditioning properties imparted by microemulsion 58B were rated as essentially equal to the hair conditioning properties imparted by FINESSE. For almost all of hair conditioning properties, the difference in average ratings between hair treated with FINESSE and hair treated with microemulsion 58B was less than the 0.3 unit differential considered in the art as significant.

Figure 6:
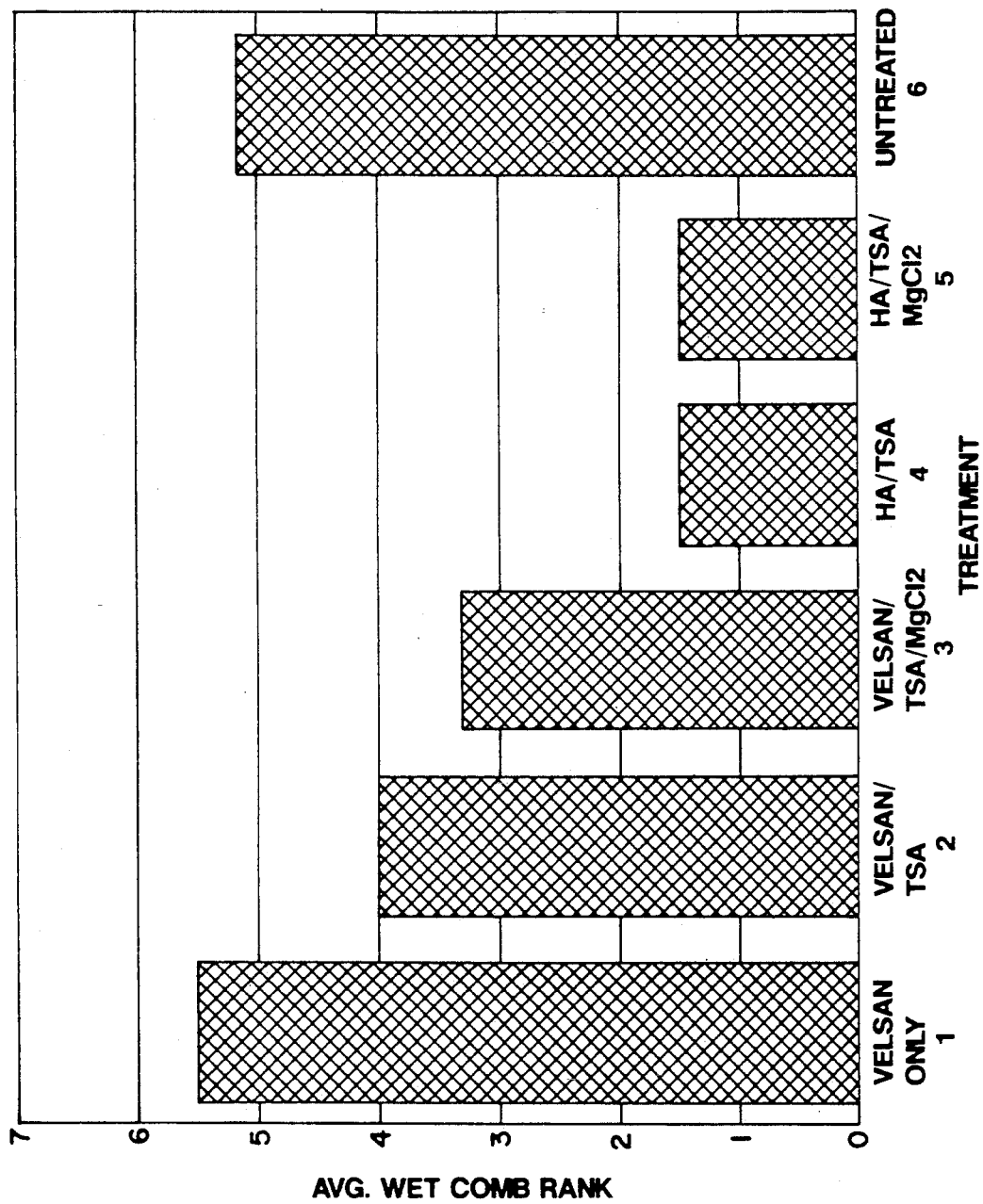
FIG. 6 is a bar graph comparing the average wet comb rank of untreated hair to hair treated with either a microemulsion composition of the present invention, compositions absent at least one of the essential ingredients of the composition of the present invention, or alcohol-water solutions including conditioning agents.

FIG. 6 is a bar graph of qualitative combing studies performed on bleached, waved hair tresses, treated with various hair treating compositions. A ranking of 1 (one) is the best-rated conditioned hair, and a rating higher than one signifies a decreasing amount of conditioning. Accordingly, it was observed that composition 58B of EX. 9, including VELSAN® P 8-3, trimethylsilylamodimethicone, and magnesium chloride (bar 3 in FIG. 6) provided significantly better conditioned hair than an untreated hair tress (bar 6); than a hair tress treated with an aqueous solution of VELSAN® P 8-3 (bar 1); and than a hair tress treated an aqueous mixture including VELSAN and trimethylsilylamodimethicone (bar 2). Accordingly, to achieve the benefits and advantages of the present invention, a microemulsion composition of the present invention includes a water-insoluble amino-containing compound, a metal ion having a valence of at least II and an ester compound having the general structural formula (II).

FIG. 6 also shows that VELSAN alone does not impart conditioning properties to the hair (bar 1), and that a metal ion having a valence of at least II is especially important in imparting improved and durable hair conditioning properties to the hair (bar 3 compared to bars 1 and 2). The isopropyl alcohol-water compositions including either an amino-functionalized silicone or an amino-functionalized silicone and a metal salt (bars 4 and 5 in FIG. 6) impart excellent conditioning properties, but are not microemulsion compositions. As previously discussed, the decreased stability of the hydroalcoholic compositions to addition of water leads to imparting more conditioning to treated hair than the stable microemulsions of the present invention.

In addition, Fourier transform infrared spectroscopy (FTIR) showed that a metal ion having a valence of at least II is needed in the microemulsion composition to achieve an improved deposition of the conditioning agents from the microemulsion onto the hair. The FTIR data showed that a composition of the present invention (bar 3 of FIG. 6) exhibited a silicone index of 1.98, whereas a composition including only VELSAN and the amino-functionalized silicone (bar 2 of FIG. 6) exhibited a silicone index of 1.38. Therefore, the metal ion having a valence of at least two improves depositions of the conditioning agents onto the hair shaft.

Figure 7:
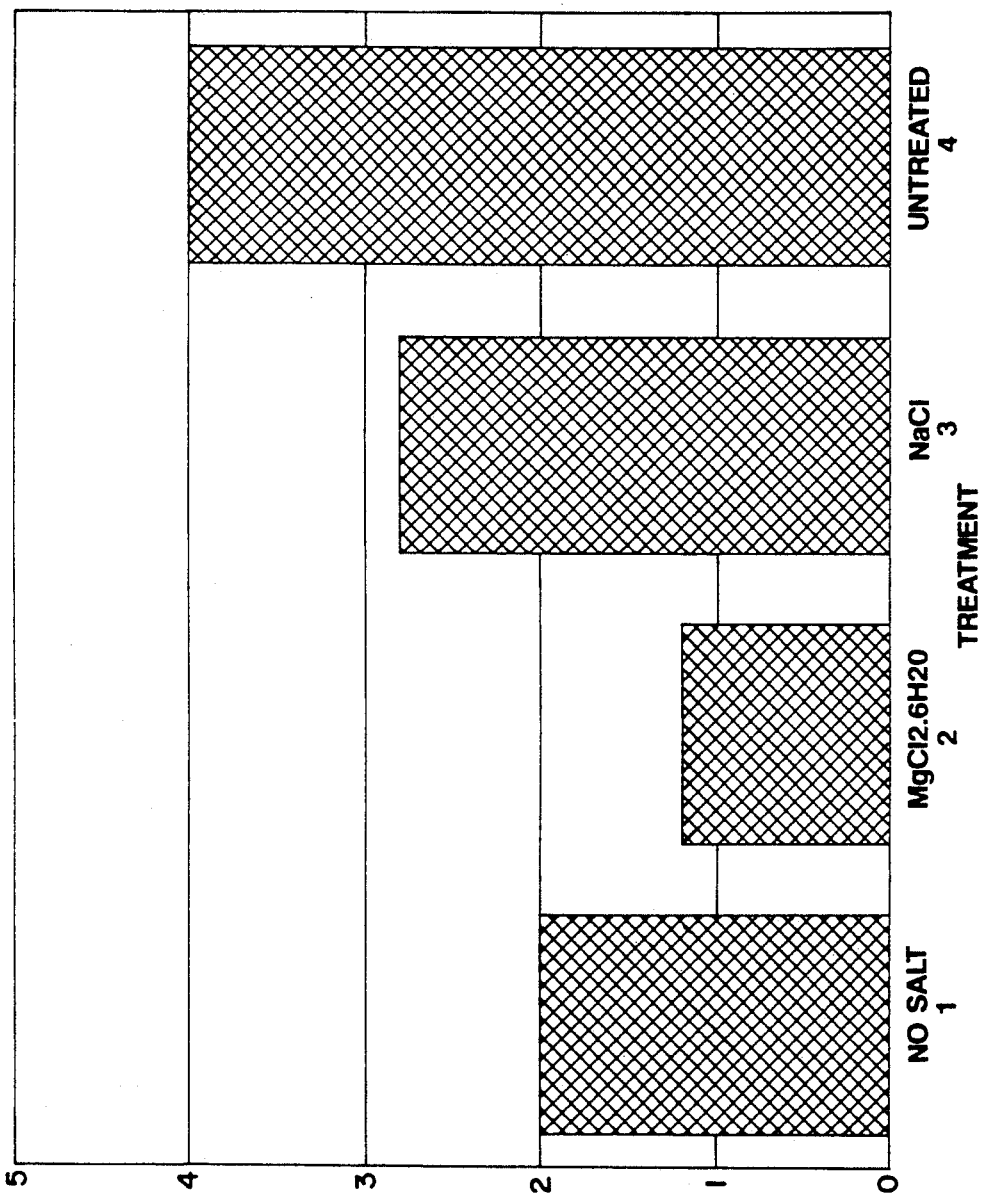
FIG. 7 is a bar graph comparing the average wet comb rank of untreated hair to hair treated with either a microemulsion composition of the present invention, a composition absent a metal salt or a composition including a monovalent metal salt.

Furthermore, FIG. 7 shows the effect of either removing a metal salt having a valence of at least II from the microemulsion composition, or using a metal salt having a valence of I. FIG. 7 demonstrates that hair treated with a composition absent a metal ion (bar 1) or with a composition including a monovalent metal ion (bar 3) does not impart the superior wet combing properties to hair imparted by microemulsion composition of the present invention including the divalent magnesium ion (bar 2). In fact, the composition including the monovalent metal ion performed more poorly than the composition absent a metal ion (bar 3 compared to bar 1).

Accordingly, the data presented in the graphs of FIGS. 1 through 7 demonstrate that the microemulsion composition performs as a conditioner, and exhibits a performance equal to the benchmark commercial conditioner FINESSE. Furthermore, it was found that the water-insoluble amino-containing compound is the primary conditioning agent, but that a metal ion having a valence of at least II is needed to improve conditioning agent deposition. In addition, an ester compound of general structural formula (II), although not acting as a conditioning agent, is needed to form the stable microemulsion of the present invention. The ability of such a stable composition to impart such improved conditioning properties to hair is both new and unexpected in the art.

In accordance with another important feature of the present invention, an optional, secondary emulsifier was added to the microemulsion composition. Accordingly, the microemulsion composition of EX. 10, was prepared by adding the ingredients in the listed order, with stirring. It was found that the amount of ester compound

EXAMPLE 10

| Microemulsion Composition with Optional Secondary Emulsifier | |
| --- | --- |
| Ingredient | % (by wt.) |
| Water, deionized | q.s. to 100% |
| PEG-78 Glyceryl Monococoate 3) | 1% |
| Isopropl $C_{12-15}$ Pareth-9 Carboxylate 1) | 3% |

| -continued | |
| --- | --- |
| Microemulsion Composition with Optional Secondary Emulsifier | |
| Ingredient | % (by wt.) |
| Trimethylsilylamodimethicone 2) | 4% |
| Magnesium Chloride Hexahydrate | 0.46% |
| Hydrochloric Acid (1$\underline{M}$) | q.s. to pH 6.5 |

3) VARONIC LI-67, Sherex Chem. Co., Inc., Dublin, OH, secondary emulsifier.

of general structural formula (II) in the microemulsion composition can be decreased when a secondary emulsifier is included, and that the conditioning properties imparted to the hair were further improved. Such a result is not unexpected in that usually a combination of emulsifiers allows the use of a lesser total amount of emulsifiers; and, as a result, because the total amount of emulsifiers is decreased, deposition of the conditioning agents on the hair is increased, as are the observed conditioning properties. In general, an optional secondary emulsifier is included in the microemulsion composition in an amount up to about 2% by weight of the composition. Suitable optional secondary emulsifiers, in addition to PEG-78 glyceryl monococoate, include, but are not limited to, PEG-200 glyceryl monotallowate, dimethicone copolyol, ethylene oxide-propylene oxide block copolymers, PEG-6000 distearate and combinations thereof.

Figure 8:
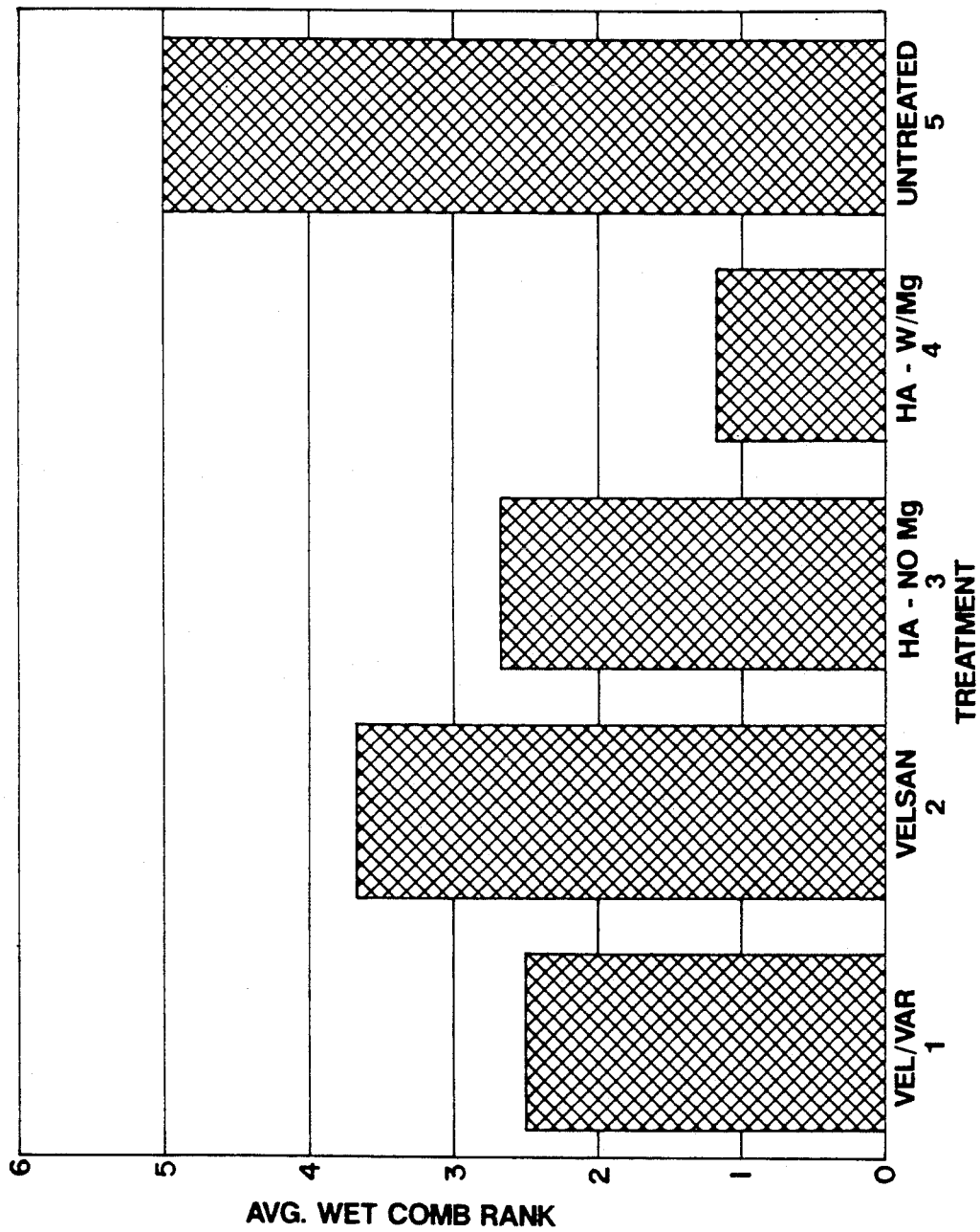
FIG. 8 is a bar graph comparing the average wet comb rank of untreated hair to hair treated with a microemulsion composition including only an ester of structural formula (II) as an emulsifier, to hair treated with a microemulsion composition including an ester of structural formula (II) and a secondary emulsifier; and to hair treated with hydroalcoholic solutions either absent or including a divalent metal ion.

FIG. 8 illustrates the conditioning properties imparted to hair treated with a composition of EX. 10 including a low amount of ester compound of general structural formula (II) and a low amount of a secondary emulsifier. Bar 1 of the bar graph of FIG. 8 shows the improved hair conditioning properties of hair treated the composition of EX. 10 over untreated hair (bar 5) and over hair treated with the microemulsion composition of EX. 9 (bar 2). Bars 3 and 4 show the hair conditioning properties imparted by a relatively unstable 50:50 isopropyl alcohol-water solution of amino-functionalized silicone (bar 3) and of amino-functionalized silicone and magnesium ion (bar 4).

Hair treated with the microemulsion compositions of EXS. 9 and 10 also were tested by FTIR. The FTIR test provides a silicone index, or the ratio of the area of the infrared peak at 1250 cm$^{-1}$ to the area of the infrared peak at 1240 cm$^{-1}$, indicating the amount of silicone conditioner compound deposited on the hair. It was found that hair treated by the microemulsion composition of EX. 9 demonstrated a silicone index of 2.65, and that hair treated by the microemulsion composition of EX. 10 demonstrated an essentially equal silicone index of 2.71. Accordingly, the microemulsion compositions of both EXS. 7 and 8 exhibit an excellent ability to deposit conditioning agent onto the hair.

In another test, a microemulsion composition (Example 11) similar to composition 58B of EX. 9 was tested for its ability to impart a variety of conditioning properties to hair. The composition of Example 11 included 4% trimethylsilylamodimethicone, 0.46% magnesium chloride, 3% isopropyl $C_{12-15}$ pareth-9 carboxylate and 1% PEG-78 glyceryl monococoate, with a pH of 3.6. Then an aerosol mousse formulation including 90% by weight the composition of EX. 11 and 10% by weight of a propellant was prepared. In this test, performed over a five day period, an individual pretreated her hair by washing with a shampoo only, avoiding all conditioning agents and styling aids. On the following day, the mousse formulation including the microemulsion composition of EX. 11 was applied to the hair. The treated hair then was evaluated the day of treatment and for three successive days. It was observed that the composition imparted significantly improved conditioning properties, including wet comb, wet feel, pull of brush, dry comb, dry feel, sheen/luster, volume and static electricity, over the pretreated hair. In a separate test, hair treated with the mousse formulation including the microemulsion composition of EX. 11 were examined by energy dispersive x-ray (EDX), and deposition of the metal salt and amino-functionalized silicone conditioning agents along the hair cuticle was observed.

The microemulsion compositions of the present invention also demonstrated an ability to impart durable conditioning properties to treated hair. For example, TABLE I tabulates the average wet comb rankings of hair treated with various conditioning compositions. A ranking of 1 (one) is the best-rated conditioned hair, and a rating higher than one signifies a decreasing amount of conditioning. In each case, freshly-shampooed hair was treated with a conditioning composition, and the wet combing property was determined subjectively by trained judges. The hair then was shampooed four times, and the average wet comb ranking was determined after each shampooing.

The data presented in TABLE I shows that untreated hair, as expected,

TABLE I

DURABILITY OF CONDITIONING PROPERTIES
IMPARTED BY MICROEMULSION COMPOSITIONS
(Avg. Wet Comb Rank)*

| Composition used to treat the hair | Number of Shampooings | | | | |
|---|---|---|---|---|---|
| | 0 | 1 | 2 | 3 | 4 |
| Untreated | 5.00 | 5.00 | 5.00 | 5.00 | 5.00 |
| Composition of EX. 10 | 3.33 | 2.50 | 3.17 | 2.83 | 3.14 |
| Composition of EX. 9 | 3.00 | 3.67 | 3.00 | 3.83 | 3.64 |
| Hydroalcoholic composition (16B) | 1.50 | 1.17 | 1.33 | 1.00 | 1.14 |
| Hydroalcoholic composition (16B), absent magnesium ion | 2.17 | 2.67 | 2.17 | 2.83 | 2.07 |

*5 = worst, 1 = best demonstrates a poor wet comb rank of 5. Similarly, the data shows that hair treated with a hydroalcoholic composition demonstrates excellent wet comb properties (rank = 1.50). Again, this result is expected because of the instability of the hydroalcoholic compositions upon the addition of water that in turn leads to enhanced deposition of the conditioning agents. The data also shows that including a metal ion having a valence of at least II improves the conditioning properties imparted to hair because the wet comb rank increased from the range of about 1-1.5 for a composition including a metal ion having a valence of II to about 2-2.8 for a composition absent the metal ion.

In regard to the microemulsion compositions of the present invention, treated hair demonstrated an improved wet comb rank of from about 3 to about 3.3 after initially treating the hair, compared to a rank of 5 for untreated hair. In addition, the conditioning properties imparted to the hair by the microemulsion composition of the present invention were observed after four shampooings and no further conditioning treatments. Imparting such improved and durable conditioning properties to the hair is both new and unexpected in the art, especially considering the stability of the microemulsion compositions of the present invention. It is surprising for microemulsion compositions that are stable upon the addition of water to so effectively deposit conditioning agents on the hair, as opposed to having the conditioning agents rinsed from the hair.

Other amino-functionalized silicones were incorporated into the microemulsion composition of EX. 10 to observe the conditioning properties imparted to treated hair by a water-insoluble amino-functionalized silicone having varying amounts of an amine functionality incorporated in the amino-functionalized silicone. The following amino-functionalized silicones, all available from Dow Corning Corp., Midland, Mich., were incorporated into the composition of EX. 10 in an amount of 4% by weight. The amount of magnesium chloride in each composition was varied to account for the differing amounts of amino-functionality present in the various amino-functionalized silicones. TABLE II illustrates the amino-functionalized silicones that were tested, and the amount of magnesium chloride included in the composition. It should be noted that the microemulsion composition including SILICONE X2-8107 was the most difficult to prepare. This observation is attributed to the fact that SILICONE X2-8107 includes a lower percentage of amino functionality than the other amino-functionalized silicones, thereby demonstrating the need for a water-insoluble amino-containing compound to achieve a microemulsion composition of the present invention.

TABLE II

Amino-functionalized Silicones
Incorporated into the Composition of EX. 10

| Amino-functionalized Silicone | % MgCl$_2$ |
|---|---|
| X2-8123 | 0.49 |
| X2-8124 | 1.47 |
| X2-8200 | 0.46 |
| X2-8120 | 1.66 |
| Q2-8220 | 0.37 |
| SOFT. CSF | 0.09 |
| X2-8107 | 0.04 |

Figure 9:
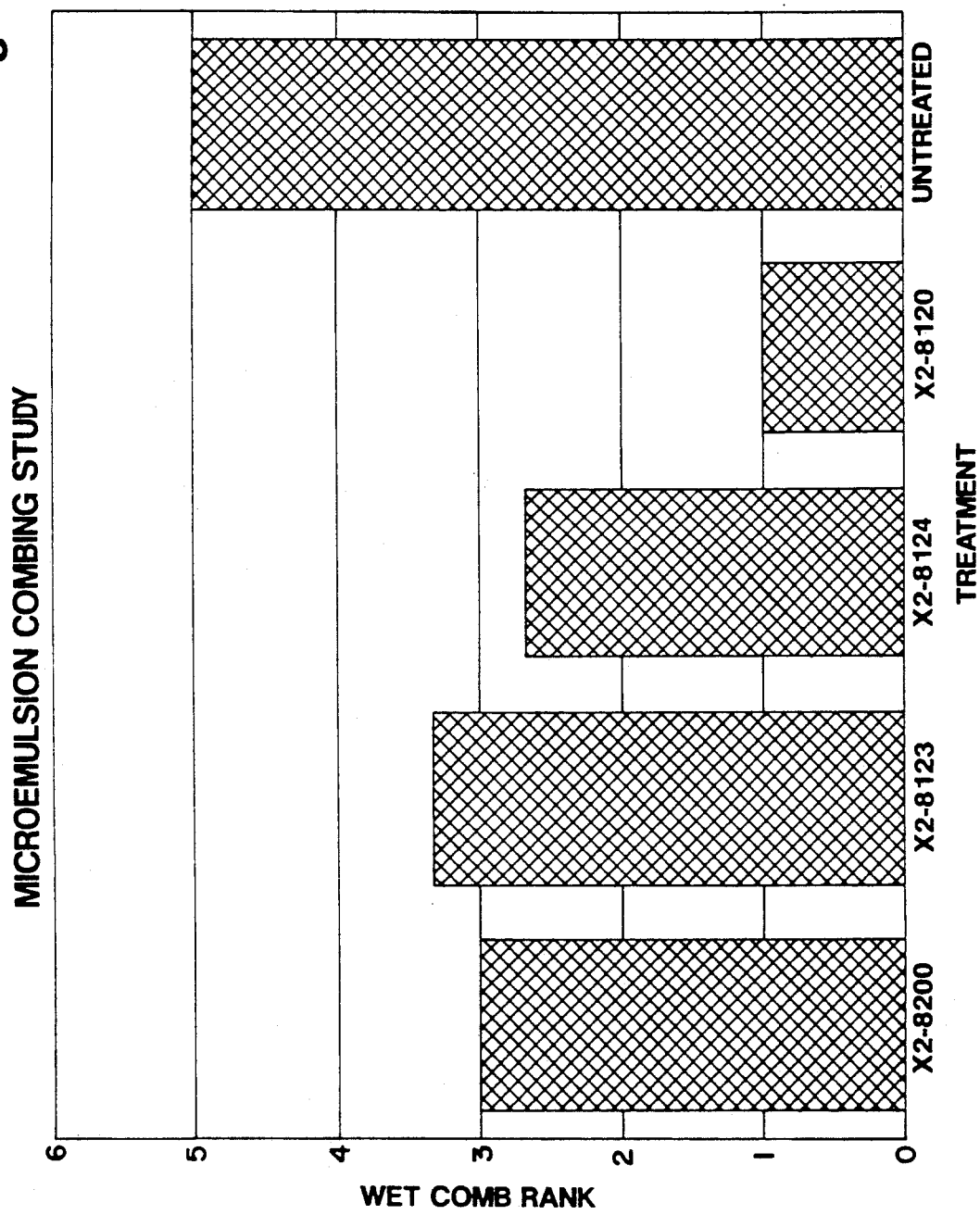
FIG. 9 is a bar graph comparing the wet comb rank of untreated hair to hair treated with microemulsion compositions including different amino-functionalized silicones.

FIG. 9 is a bar graph illustrating that each amino-functionalized silicone substantially improved the hair-conditioning property of wet combing over untreated hair. Furthermore, an FTIR study showed that each amino-functionalized silicone was sufficiently deposited on the hair because the silicone index varied only from 2.35 to 2.73 for hair treated with microemulsion compositions including different amino-functionalized silicones. Accordingly, it has been demonstrated that the microemulsion compositions of the present invention perform excellently as hair conditioners, with the water-insoluble amino-containing compound serving as the primary conditioner and the metal salt providing further improved conditioning properties. In addition, it has been found that the ester compound serves as an emulsifier, not a conditioning agent; and, as the amount of ester compound in the composition decreases, such as when an optional secondary emulsifier is included, that hair conditioning properties further improve. However, the ester compound of general structural formula (II) is an essential ingredient to provide a stable, translucent microemulsion composition.

In accordance with another important feature of the present invention, the microemulsion composition also can include anionic, nonionic or amphoteric surfactants to provide a hair shampoo-conditioner product. For example, sodium lauryl sulfate and lauramide DEA, in amounts of about 10% and 3% by weight of the composition respectively, were incorporated into a microemulsion composition of EX. 6 to provide a hair shampoo-conditioner composition. The resulting compositions, both thickened and unthickened, were applied to hair, and the treated hair was evaluated by panelist combing and by instrumentation for hair conditioning properties.

The bar graphs of FIG. 10 show that a base shampoo including 10% by weight sodium lauryl sulfate and 3% by weight lauramide DEA (bar 1) exhibited a poor average wet comb ranking of almost 5. Adding a water-insoluble amino-containing compound, and an ester compound of general structural formula (II), to the base shampoo (bar 2) improved the wet combing to slightly above 4. Further adding a metal ion (either divalent (bar 3) or monovalent (bar 4)) further improved the wet comb rank to between 2 and 3. A microemulsion composition of the present invention without the added cleansing surfactants (bar 5) was included for comparison and demonstrated an average wet comb rank of slightly greater than 1. Therefore, as expected, the microemulsion composition more efficiently deposits the conditioning agents on the hair because the conditioning agents are not rinsed from the hair with the anionic and nonionic cleansing surfactants; however, the shampoo composition including the microemulsion composition demonstrated excellent conditioning properties for a shampoo-conditioner product. It is theorized that the further improved conditioning properties observed for the shampoo-conditioner including a monovalent metal is because the decreased stability of the microemulsion composition including the monovalent metal, and therefore the increased deposition of conditioning agents from the less stable composition.

FIG. 11 illustrates the improved conditioning properties imparted to hair treated with a shampoo-conditioner including 10% sodium lauryl sulfate, 3% lauramide DEA and a microemulsion composition of the present invention including 4% of a trimethylsilylamodimethicone, 4% of isopropyl pareth-9 carboxylate and 0.46% magnesium chloride. Various compositions, including different trimethylsilylamodimethicones, were prepared and applied to the hair. Then the treated hair was compared to hair shampooed with PERT PLUS, a commercially-available shampoo-conditioner, from Proctor & Gamble Co., Cincinnati, Ohio, and recognized as a premium hair shampoo-conditioner. The bar graphs of FIG. 11 show that the hair shampoo conditioners including the microemulsion of the present invention impart wet combing conditioning properties to hair that equal or surpass the conditioning properties imparted by PERT PLUS. Imparting such excellent hair conditioning properties from an anion hair shampoo-conditioner composition is unexpected in view of the stability of the microemulsion composition of the present invention.

To further demonstrate that the stable microemulsion compositions of the present invention effectively deposit conditioning agents on the hair, the following compositions of EXS. 12-22 were prepared and applied to normal brown tresses of hair. The treated hair then was tested by Diffuse Reflectance Infrared Fourier Transform Spectroscopy (DRIFTS) to determine the relative amount of conditioning agent deposited on tresses treated with compositions including a trimethylsilylamodimethicone, with and without magnesium chloride, and various levels of other ingredients.

| EX. | Trimethylsilyl-amodimethicone | Isopropyl Pareth-9 Carboxylate | MgCl.6H$_2$O |
|---|---|---|---|
| 12 | -0- | 7.0 | -0- |
| 13 | 4.0 | 7.0 | -0- |
| 14 | 4.0 | 7.0 | .46 |
| 15 | 4.0 | -0- | -0- |
| 16 | 4.0 | -0- | .46 |
| 17 | -0- | -0- | -0- |
| 18 | -0- | -0- | -0- |
| 19 | 4.0 | 4.0 | -0- |
| 20 | 4.0 | 4.0 | .46 |
| 21 | 4.0 | 4.0 | -0- |
| 22 | 4.0 | 7.0 | .46 |

Ingredients (wt. % in water)

| EX. | NaCl | Lauramide DEA | Sodium Lauryl Sulfate 30% | Isopropyl Alcohol |
|---|---|---|---|---|
| 12 | -0- | -0- | -0- | -0- |
| 13 | -0- | -0- | -0- | -0- |
| 14 | -0- | -0- | -0- | -0- |
| 15 | -0- | -0- | -0- | 48% |
| 16 | -0- | -0- | -0- | 48% |
| 17 | -0- | -0- | -0- | -0- |
| 18 | -0- | 3.0 | 50.0 | -0- |
| 19 | -0- | 3.0 | 50.0 | -0- |
| 20 | -0- | 3.0 | 50.0 | -0- |
| 21 | .46 | 3.0 | 50.0 | -0- |
| 22 | -0- | -0- | -0- | -0- |

The tresses used to test the compositions of EXS. 12 through 17 were washed with a 12% active sodium lauryl sulfate solution before treatment. The tress used to test the composition of EX. 22 was washed with a 15% sodium lauryl sulfate solution before treatment. After a hair tress was treated with a composition of EXS. 12-22, the ratio of the area of the silicon-methyl (SiMe) infrared peak at 1260 cm$^{-1}$ to the area of the Amide III infrared peak at 1240 cm$^{-1}$ of hair keratin, and used as the internal standard, was calculated for each hair tress using the second derivative spectrum. These ratios, or silicone indexes, are correlated to ppm silicon deposited on tresses, as determined by atomic absorption spectroscopy, with a linear correlation from 40 ppm to 170 ppm silicon. The calculated silicone indexes and the corresponding ppm silicon are summarized in Table III.

TABLE III

| Example | Silicone Index* | ppm Silicone |
|---|---|---|
| 12 | 0 | 0 |
| 13 | 1.38 | 42.12 |
| 14 | 1.98 | 148.3 |
| 15 | 2.12 | 163.7 |
| 16 | 2.43 | 197.7 |
| 17 | 0 | 0 |
| 18 | 0 | 0 |
| 19 | 0 | 0 |
| 20 | 0 | 0 |
| 21 | 0 | 0 |
| 22 | 1.46 | 91.2 |

*Silicone Index = $\dfrac{\text{Area of SiMe peak at 1260 cm}^{-1}}{\text{Area of Amide III peak at 1240 cm}^{-1}}$ The data in TABLE III demonstrate the excellent deposition of a conditioning agent onto the hair from a microemulsion composition of the present invention (EX. 14). However, it was surprising that a detectable deposition of conditioning agent on the tress treated with the hair shampoo/conditioner composition of 20 was not observed. Therefore, a tress treated with PERT PLUS shampoo was tested using the DRIFTS method of FTIR because PERT PLUS is a well-known, commercial shampoo-conditioner. The silicone index for the PERT PLUS treated tress also was 0, indicating that no conditioning agent deposition is detected. Silicone Indexes were also calculated from the infrared spectra obtained in tests using tresses treated 3 times and 25 times with PERT PLUS. The Silicone Index of the tress treated 3 times corresponded to 63 ppm silicon deposition and treated 25 times corresponded to 114 ppm silicon deposition. Overall, the DRIFTS data indicates that there is no detectable deposition of conditioning agents on tresses treated with a microemulsion composition incorporated into a shampoo base. However, this method also detected no deposition of silicone on a tress treated once with PERT PLUS shampoo. But, even though conditioning agent deposition was not detected, the treated hair demonstrated improved conditioning properties.

There are several commercial products in the marketplace to improve the conditioning properties of hair. However, in accordance with the method of the present invention, contacting the hair with a stable microemulsion composition including an amino-containing compound, an ionizable metal salt and an ester compound of general structural formula (II) conditions the hair and imparts conditioning properties that are unexpectedly durable. As a result, the microemulsion composition, as a conditioner, does not need to be reapplied to the hair after each shampooing, therefore making hair treatment more convenient for the consumer.

Consequently, the method and microemulsion composition of the present invention impart exceptional hair conditioning properties to treated hair usually demonstrated only by premium hair conditioner compositions. It is both surprising and unexpected for a microemulsion composition of the present invention, including a water-insoluble amino-containing compound, to be a consumer-appealing translucent product, to maintain product stability over long storage times, and to impart such excellent and durable hair conditioning properties to treated hair. The microemulsion compositions of the present invention both effectively deposit conditioning agents on the hair effectively and are especially easy to rinse from the hair. Consequently, the effective deposition of conditioners on the hair requires less microemulsion composition to be applied to the hair, thereby also reducing the amount of dulling, chemical residue that coats the hair shaft.

In addition, the method of the present invention provides the further benefits of durable conditioning; not leaving the hair tacky or sticky; not forming a crust and therefore providing combability; and providing manageable and styleable hair having body. In addition, after treating the hair with the composition of the present invention, the hair feels natural and thickened, has body, is soft, shiny, manageable, and combable. Further, the benefits afforded by the composition of the present invention are achieved regardless of whether the composition is applied in a rinse-off or a leave-on fashion. These beneficial effects can be achieved by using an aqueous spray formulation, shampoo-conditioner formulation, shampoo formulation or other suitable hair treatment product.

Obviously, many modifications and variations of the invention as hereinbefore set forth can be made without departing from the spirit and scope thereof and therefore only such limitations should be imposed as are indicated by the appended claims.

We claim:

1. A hair-treating composition to impart hair conditioning properties to treated hair comprising from about 0.1% to about 6% by weight of a water-insoluble amino-containing compound having a water solubility of 0.5 g or less per 100 milliliters of water, the water-insoluble amino-containing compound selected from the group consisting of:
a) a monomeric primary amine, a monomeric secondary amine of a monomeric tertiary amine having the structure

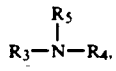

wherein when the amino-containing compound is a primary amine, $R_3$ is an alkyl group or substituted alkyl group of between five and about 20 carbon atoms in length, and $R_4$ and $R_5$ are hydrogen atoms; when the amino-containing compound is a secondary amine, $R_3$ and $R_4$ are alkyl groups or substituted alkyl groups of about 20 or less carbon atoms in length and wherein either $R_3$ or $R_4$ is at least five carbon atoms in length, and $R_5$ is a hydrogen atom; and when the amino-containing compound is a tertiary amine, $R_3$, $R_4$ and $R_5$ are alkyl groups or substituted alkyl groups of about 20 or less carbon atoms in length and wherein either $R_3$, $R_4$ or $R_5$ is at least five carbon atoms in length,
b) a diamine or an amino-containing polymer including primary or secondary amino-functionalities,
c) a trimethylsilylamodimethicone having the structure

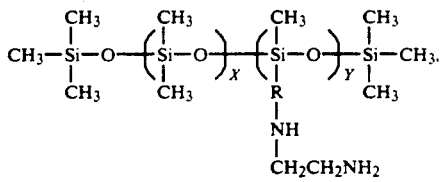

wherein $X+Y$ is a number from about 50 to about 500, and the mole % amine functionality varies from about 0.7% to about 8%, and wherein R is an alkyl group having from 2 to 5 carbon atoms, and
d) combinations thereof; from about 0.005% to about 4% by weight of an ionizable metal salt, wherein the metal of the ionizable metal salt has a valence of at least II; an ester compound having the formula $R_1—O—(A)_x CH_2 CO_2 R_2$, wherein $R_1$ is an alkyl group including from about 8 to about 18 carbon atoms, $R_2$ is an alkyl group including from one to about four carbon atoms, A is an alkylene oxide moiety wherein the alkylene group includes from one to about four carbon atoms and X is a number in the range of from about 4 to about 20, wherein the ester compound has an HLB value of from about 10 to about 20 and wherein the ester compound is present in an amount ranging from about 0.2% to about 15% by weight of the composition and in a ratio of the amount of ester compound to the amount of the water-insoluble amino-containing compound of at least about 0.75 to 1; and water; wherein the composition has a pH of less than 7.

2. The composition of claim 1 wherein the water-insoluble amino-compound is a monomeric primary amine, wherein R₃ is an alkyl group or a substituted alkyl group of between five and about 20 carbon atoms in length, and R₄ and R₅ are hydrogen atoms.

3. The composition of claim 1 wherein the water-insoluble amino compound is a monomeric secondary amine, wherein R₃ and R₄ are alkyl groups or substituted alkyl groups of about 20 or less carbon atoms in length, and wherein either R₃ or R₄ is at least five carbon atoms in length, and R₅ is a hydrogen atom.

4. The composition of claim 1 wherein the water-insoluble amino-compound is a monomeric tertiary amine, wherein R₃, R₄ and R₅ are alkyl groups or substituted alkyl groups of about 20 or less carbon atoms in length, and wherein either R₃, R₄ or R₅ is at least five carbon atoms in length.

5. The composition of claim 1 wherein the water-insoluble amino-containing compound is selected from the group consisting of octylamine, dioctylamine, trioctylamine, dimethyloctylamine, pentylamine, dipentylamine, hexylamine, dihexylamine, trihexylamine, heptylamine, dodecylamine, hexadecylamine, dilaurylmethylamine, octadecylamine, tallow amine, hydrogenated-tallow amine, di(hydrogenated-tallow) amine, tri(hydrogenated-tallow) amine, oleyl amine, soya amine, cocamine, dicocamine, methyl dicocamine, dimethylcocamine, dimethyldodecylamine, dimethyltetradecylamine, dimethylhexadexylamine, dimethyltallowamine, dimethyloleylamine, dimethylsoyamine, tridodecylamine, methyl stearylamine and mixtures thereof.

6. The composition of claim 1 wherein the water-insoluble amino-containing polymer is a water-insoluble ethoxylated amine.

7. The composition of claim 1 wherein the trimethylsilylamodimethicone has the structure

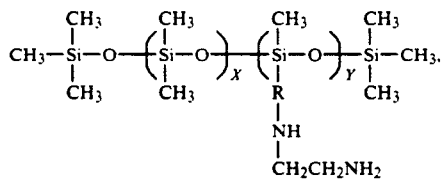

wherein X+Y is a number from about 100 to about 300, and the mole % amine functionality varies from about 2% to about 6%, and wherein R is an alkyl group having from 2 to 5 carbon atoms.

8. The composition of claim 1 wherein the water-insoluble amino-containing compound is selected from the group consisting of octylamine, pentylamine, dipentylamine, trimethylsilylamodimethicone, dodecylamine, dilaurylmethylamine, dioctylamine, trioctylamine, cocamine, hydrogenated-tallow amine, di(hydrogenated-tallow) amine, tri(hydrogenated-tallow) amine and combinations thereof.

9. The composition of claim 1 wherein the metal of the ionizable metal salt is selected from the group consisting of magnesium, calcium, barium, aluminum, titanium, vanadium, manganese, mercury, cadmium, lead, iron, cobalt, nickel, silver, copper, cerium, hafnium, germanium, zinc, zirconium and combinations thereof.

10. The composition of claim 1 wherein the ionizable metal salt is selected from the group consisting of aluminum chloride, magnesium chloride, zinc chloride, ferric chloride, calcium sulfate; and combinations thereof.

11. The composition of claim 1 wherein the ionizable metal salt and the water-insoluble amino-containing compound are present in a molar or molar-equivalent ratio of at least 1:1.

12. The composition of claim 1 wherein R₁ of the ester compound is a linear alkyl group including from about 10 to about 16 carbon atoms; R₂ of the ester compound is an alkyl group including two or three carbon atoms; A is an ethylene oxide moiety; and X is a number in the range of from about 7 to about 15.

13. The composition of claim 1 wherein the ester compound is isopropyl C₁₂-C₁₅ pareth-9 carboxylate.

14. The composition of claim 1 wherein the water-insoluble amino-containing compound is present in an amount ranging from about 1% to about 4% by weight; the ionizable metal salt is present in an amount ranging from about 0.01% to about 2% by weight an the ester compound is present in an amount ranging from about 2% to about 10% by weight.

15. The composition of claim 1 wherein the pH is in the range of from about 3.0 to about 6.8.

16. The composition of claim 1 wherein the water-insoluble amino-containing compound is trimethylsilylamodimethicone; the ionizable metal salt is magnesium chloride; and the ester compound is iospropyl C₁₂-C₁₅ pareth-9 carboxylate.

17. The composition of claim 1 wherein the composition further comprises up to about 2% by weight of a secondary emulsifier selected from the group consisting of PEG-78 glyceryl monococoate, PEG-200 glyceryl monotallowate, dimethicone copolyol, ethylene oxide-propylene oxide block copolymers, PEG-6000 distearate and combinations thereof.

18. The composition of claim 1 wherein the ionizable metal salt includes an anion that is organic or inorganic in chemical structure.

19. The composition of claim 18 wherein the anion of the ionizable metal salt is selected from the group consisting of chloride, bromide, sulfate, nitrate, phosphate, acetate, lactate and combinations thereof.

20. The composition of claim 1 wherein the composition further comprises a sufficient amount of a water-soluble polymeric compound to fix the treated hair in a predetermined hair style.

21. The composition of claim 20 wherein the polymeric compound is selected from the group consisting of polyvinylpyrrolidone, sodium polystyrenesulfonate vinylpyrrolidone-methacrylic acid copolymer, vinylpyrrolidone-vinyl acetate copolymer, vinylmethyl ether-vinylpyrrolidone copolymer, vinylmethyl ether-maleic acid copolymer, vinyl pyrrolidone-dimethylaminoethylmethacrylate copolymer, and combinations thereof.

22. The composition of claim 1 wherein the composition further comprises up to about 25% active basis by weight of the composition of a cleansing surfactant to cleanse the treated hair.

23. The composition of claim 22 wherein the cleansing surfactant is an anionic surfactant, a nonionic surfactant, an amphoteric surfactant or a combination thereof.

24. The composition of claim 23 wherein the anionic surfactant is an alkali metal salt, an ammonium salt, an alkylammonium salt or a hydroxyalkylammonium salt of a fatty acid, a fatty alcohol sulfate, a polyethoxylated fatty alcohol sulfate, an alkylbenzene sulfonate, an alkylarylpolyether sulfate or combinations thereof, wherein the fatty moiety includes from twelve to eighteen carbon atoms and the alkyl moiety includes from twelve to eighteen carbon atoms.

25. The composition of claim 23 wherein the anionic surfactant is selected from the group consisting of sodium lauryl sulfate, ammonium lauryl sulfate, triethanolammonium lauryl sulfate, sodium lauryl ether sulfate, ammonium lauryl ether sulfate, triethanolammonium lauryl ether sulfate and combinations thereof.

26. The composition of claim 23 wherein the nonionic surfactant is selected from the group consisting of a polyethoxylated alkylphenol, a polypropoxylated alkylphenol, a polyhydroxylated polyether of a fatty alcohol, a fatty alkanolamide or a combination thereof, wherein the alkyl moiety includes at least eight carbon atoms and the fatty moiety includes from twelve to eighteen carbon atoms.

27. The composition of claim 26 wherein the alkanolamide is selected from the group consisting of lauramide DEA, lauramide MEA, cocamide DEA, cocamide MEA, capramide DEA, ricinoleamide DEA, soyamide DEA, myristamide DEA, stearamide DEA, oleylamide DEA, tallowamide DEA, lauramide MIPA, stearamide MEA, tallowamide MEA, isostearamide DEA, isostearamide MEA, myristamide MEA and combinations thereof.

28. A method of treating hair to impart hair conditioning properties to the hair comprising contacting the hair with a composition comprising from about 0.1% to about 6% by weight of water-insoluble amino-containing compound having a water solubility of 0.5 g or less per 100 milliliters of water, the water-insoluble amino-containing compound selected from the group consisting of:

a) a monomeric primary amine, a monomeric secondary amine or a monomeric tertiary amine having the structure

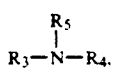

wherein when the amino-containing compound is a primary amine, $R_3$ is an alkyl group or substituted alkyl group of between five and about 20 carbon atoms in length, and $R_4$ and $R_5$ are hydrogen atoms; when the amino-containing compound is a secondary amine, $R_3$ and $R_4$ are alkyl groups or substituted alkyl groups of about 20 or less carbon atoms in length and wherein either $R_3$ or $R_4$ is at least five carbon atoms in length, and $R_5$ is a hydrogen atom; and when the amino-containing compound is a tertiary amine, $R_3$, $R_4$ and $R_5$ are alkyl groups or substituted alkyl groups of about 20 or less carbon atoms in length and wherein either $R_3$, $R_4$ or $R_5$ is at least five carbon atoms in length, b) a diamine or an amino-containing polymer including primary or secondary amino-functionalities, c) a trimethylsilylamodimethicone having the structure

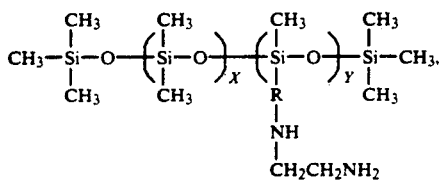

wherein X+Y is a number from about 50 to about 500, and the mole % amine functionality varies from about 0.7% to about 8%, and wherein R is an alkyl group having from 2 to 5 carbon atoms, and d) combinations thereof; from about 0.005% to about 4% by weight of an ionizable metal salt, wherein the metal of the ionizable metal salt has a valence of at least II; an ester compound having the formula $R_1-O-(A)_xCH_2CO_2R_2$, wherein $R_1$ is an alkyl group including from about 8 to about 18 carbon atoms, $R_2$ is an alkyl group including from one to about four carbon atoms, A is an alkylene oxide moiety wherein the alkylene group includes from one to about four carbon atoms and X is a number in the range of from about 4 to about 20, wherein the ester compound has an HLB value of from about 10 to about 20 and wherein the ester compound is present in an amount ranging from about 0.2% to about 15% by weight of the composition and in a ratio of the amount of the ester compound to the amount of the water-insoluble amino-containing compound of at least about 0.75 to 1; and water; wherein the composition has a pH of less than 7.

29. The method of claim 28 wherein the water-insoluble amino-compound is a monomeric primary amine, wherein $R_4$ is an alkyl group or a substituted alkyl group of between five and about 20 carbon atoms in length, and $R_4$ and $R_5$ are hydrogen atoms.

30. The method of claim 28 wherein the water-insoluble amino-compound is a secondary amine, wherein $R_3$ and $R_4$ are alkyl groups or substituted alkyl groups of about 20 or less carbon atoms in length, and wherein either $R_3$ or $R_4$ is at least five carbon atoms in length, and $R_5$ is a hydrogen atom.

31. The method of claim 28 wherein the water-insoluble amino-compound is a tertiary amine, wherein $R_3$, $R_4$ and $R_5$ are alkyl groups or substituted alkyl groups of about 20 or less carbon atoms in length, and wherein either $R_3$, $R_4$ or $R_5$ is at least five carbon atoms in length.

32. The method of claim 28 wherein the water-insoluble amino-containing compound is selected from the group consisting of octylamine, dioctylamine, trioctylamine, dimethyloctylamine, pentylamine, dipentylamine, hexylamine, dihexylamein, trihexylamine, heptylamine, dodecylamine, hexadecylamine, dilaurylmethylamine, octadecylamine, tallow amine, hydrogenated-tallow amine, di(hydrogenated-tallow) amine, tri(hydrogenated-tallow) amine, oleyl amine, soya amine, cocamine, dicocamine, methyl dococamine, dimethylcocamine, dimethyldodecylamine, dimethyltetradecylamine, dimethylhexadecylamine, dimethyltallowamine, dimethyloleylamine, dimethylsoyamine, tridodecylamine, methyl stearylamine and combinations thereof.

33. The method of claim 28 wherein the water-insoluble amino-containing polymer is a water-insoluble ethoxylated amine.

34. The method of claim 28 wherein the trimethylsilylamodimethicone has the structure:

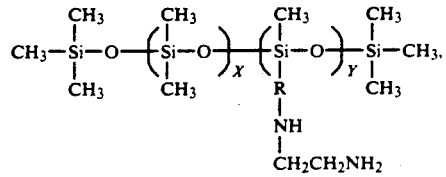

wherein X+Y is a number from about 100 to about 300, and the mole % amine functionality varies from about 2% to about 6%, and wherein R is an alkyl group having from 2 to 5 carbon atoms.

35. The method of claim 28 wherein the water-insoluble amino-containing compound is selected from the group consisting of octylamine, pentylamine, dipentylamine, water-insoluble ethoxylated amines, trimethylsilylamodimethicone, dioctylamine, dodecylamine, dilaurylmethylamine, trioctylamine, cocamine, hydrogenated-tallow amine, di(hydrogenated-tallow) amine, and tri(hydrogenated-tallow) amine and combinations thereof.

36. The method of claim 28 wherein the metal of the ionizable metal salt is selected from the group consisting of magnesium, aluminum, calcium, barium, titanium, vanadium, manganese, mercury, cadmium, lead, iron, cobalt, nickel, silver, copper, cerium, hafnium, germanium, zinc, zirconium and combinations thereof.

37. The method of claim 28 wherein the ionizable metal salt is selected from the group consisting of aluminum chloride, aluminum sulfate, aluminum lactate, copper chloride, magnesium chloride, zinc chloride, ferric chloride, calcium sulfate and mixtures thereof.

38. The method of claim 28 wherein the ionizable metal salt and water-insoluble amino-containing compound are present in a molar or molar-equivalent ratio of at least 1:1.

39. The method of claim 28 wherein $R_1$ of the ester compound is a linear alkyl group including from about 10 to about 16 carbon atoms; $R_2$ of the ester compound is an alkyl group including two or three carbon atoms; A is an ethylene oxide moiety; and X is a number in the range of from about 7 to about 15.

40. The method of claim 28 wherein the ester compound is isopropyl $C_{12}$-$C_{15}$ pareth-9 carboxylate.

41. The method of claim 28 wherein the water-insoluble amino-containing compound is present in an amount ranging from about 1% to about 4% by weight; the ionizable metal salt is present in an amount ranging from about 0.01% to about 2% by weight and the ester compound is present in an amount ranging from about 2% to about 10% by weight.

42. The method of claim 28 wherein the pH is in the range of from about 3.0 to about 6.8.

43. The method of claim 28 wherein the water-insoluble amino-containing compound is trimethylsilylamodimethicone; the ionizable metal salt is magnesium chloride; and the ester compound is isopropyl $C_{12}$-$C_{15}$ pareth-9 carboxylate.

44. The method of claim 28 wherein the composition further comprises up to about 2% by weight of a secondary emulsifier selected from the group consisting of PEG-89 glyceryl monococoate, PEG-200 glyceryl monotallowate, dimethicone polyol, ethylene oxide-propylene oxide block copolymers, PEG-6000 distearate and combinations thereof.

45. The method of claim 28 wherein the ionizable metal salt includes an anion that is organic or inorganic in chemical structure.

46. The method of claim 45 wherein the anion of the ionizable metal salt is selected from the group consisting of chloride, bromide, sulfate, nitrate, phosphate, acetate and lactate; or mixtures thereof.

47. The method of claim 28 wherein the composition further comprises a sufficient amount of a water-soluble polymeric compound to fix the treated hair in a predetermined hair style.

48. The method of claim 47 wherein the polymeric compound is polyvinylpyrrolidone, sodium polystyrenesulfonate polyvinylpyrrolidone, sodium polystyrenesulfonate vinylpyrrolidone-methacrylic acid copolymer, vinylpyrrolidone-vinyl acetate copolymer, vinylmethyl ether-vinylpyrrolidone copolymer, vinylmethyl ether-maleic acid copolymer, vinyl pyrrolidone-dimethylaminoethylmethacrylate copolymer, and combinations thereof.

49. The method of claim 28 wherein the composition further comprises up to about 25% active basis by weight of the composition of a cleansing surfactant to cleanse the treated hair.

50. The method of claim 49 wherein the cleansing surfactant is an anionic surfactant, a nonionic surfactant, an amphoteric surfactant or a combination thereof.

51. The method of claim 50 wherein the anionic surfactant is an alkali metal salt, an ammonium salt, an alkylammonium salt or a hydroxyalkylammonium salt of a fatty acid, a fatty alcohol sulfate, a polyethoxylated fatty alcohol sulfate, an alkylbenzene sulfonate, an alkylarylpolyether sulfate or combinations thereof wherein the fatty moiety includes from twelve to eighteen carbon atoms and the alkyl moiety includes from twelve to eighteen carbon atoms.

52. The method of claim 50 wherein the anionic surfactant is selected from the group consisting of sodium lauryl sulfate, ammonium lauryl sulfate, triethanolammonium lauryl sulfate, sodium lauryl ether sulfate, ammonium lauryl ether sulfate, tricthanolammonium lauryl ether sulfate and combinations thereof.

53. The method of claim 50 wherein the nonionic surfactant is selected from the group consisting of a polyethoxylated alkylphenol, a polypropoxylated alkylphenol, a polyhydroxylated polyether of a fatty alcohol, a fatty alkanolamide or a combination thereof, wherein the alkyl moiety includes at least eight carbon atoms and the fatty moiety includes from twelve to eighteen carbon atoms.

54. The method of claim 53 wherein the alkanolamide is selected from the group consisting of lauramide DEA, lauramide MEA, cocamide DEA, cocamide MEA, capramide DEA, ricinoleamide DEA, soyamide DEA, myristamide DEA, stearamide DEA, oleylamide DEA, tallowamide DEA, lauramide MIPA, stearamide MEA, tallow amide MEA, isostearamide DEA, isostearamide MEA, myristamide MEA and combinations thereof.

* * * * *